United States Patent
Wiles et al.

(10) Patent No.: US 9,125,904 B1
(45) Date of Patent: Sep. 8, 2015

(54) BIPHENYL IMIDAZOLES AND RELATED COMPOUNDS USEFUL FOR TREATING HCV INFECTIONS

(75) Inventors: Jason Allan Wiles, Hamden, CT (US); Venkat Gadhachanda, Hamden, CT (US); Dawei Chen, Middletown, CT (US); Qiuping Wang, Bethany, CT (US); Akihiro Hashimoto, Branford, CT (US); Godwin Pais, Hamden, CT (US); Xiangzhu Wang, Madison, CT (US); Milind Deshpande, Madison, CT (US); Avinash Phadke, Branford, CT (US)

(73) Assignee: ACHILLION PHARMACEUTICALS, INC., New Haven, CT (US)

( * ) Notice: Subject to any disclaimer, the term of this patent is extended or adjusted under 35 U.S.C. 154(b) by 282 days.

(21) Appl. No.: 13/105,504

(22) Filed: May 11, 2011

Related U.S. Application Data

(60) Provisional application No. 61/421,426, filed on Dec. 9, 2010, provisional application No. 61/352,137, filed on Jun. 7, 2010, provisional application No. 61/333,591, filed on May 11, 2010.

(51) Int. Cl.
| | |
|---|---|
| *A61K 31/44* | (2006.01) |
| *A61K 31/47* | (2006.01) |
| *A61K 38/05* | (2006.01) |
| *A61K 31/439* | (2006.01) |
| *A61K 31/4709* | (2006.01) |

(52) U.S. Cl.
CPC ........... *A61K 31/439* (2013.01); *A61K 31/4709* (2013.01); *A61K 38/05* (2013.01)

(58) Field of Classification Search
CPC ............ A61K 31/439; A61K 31/4709; A61K 2300/00; A61K 38/05
USPC ......................... 514/312, 299, 397
See application file for complete search history.

(56) References Cited

U.S. PATENT DOCUMENTS

| 6,448,392 | B1 | 9/2002 | Hostetler et al. | |
|---|---|---|---|---|
| 6,599,887 | B2 | 7/2003 | Hostetler et al. | |
| 7,749,983 | B2 | 7/2010 | Hostetler et al. | |
| 2008/0050336 | A1 | 2/2008 | Bachand et al. | |
| 2009/0048297 | A1* | 2/2009 | Phadke et al. | 514/314 |
| 2010/0158862 | A1 | 6/2010 | Kim et al. | |
| 2010/0310512 | A1 | 12/2010 | Guo et al. | |
| 2011/0064698 | A1* | 3/2011 | Or et al. | 424/85.5 |

FOREIGN PATENT DOCUMENTS

| WO | 2008021927 A2 | 2/2008 |
|---|---|---|
| WO | 2010111483 A1 | 9/2010 |
| WO | 2010132601 A1 | 11/2010 |
| WO | 2011031904 A1 | 3/2011 |
| WO | 2011091532 A1 | 8/2011 |

OTHER PUBLICATIONS

Hepatitis C New Drug Research and Liver Health.( http://hepatitiscnewdrugresearch.com/sovaprevir-formerly-ach-1625.html).*
STN registration file RN 1001667-23-7 Sovaprevir.*
Prichard & Shipman, "A three-Dimensional Model to Analyze Drug-Drug Interactions," Antiviral Research, 14, (1990), 181-206.
Prichard et al., "Strategic Design and Three-Dimensional Analysis of Antiviral Drug Combinations," Antimicrobial Agents and Chemotherapy, 37(3), (1993), 540-545.
Prichard, "Analysis of Combinations of Antiviral Drugs and Design of Effective Multidrug Therapies," Antiviral Therapy, 1, (1996), 9-20.

* cited by examiner

*Primary Examiner* — Shengjun Wang
(74) *Attorney, Agent, or Firm* — Cantor Colburn LLP

(57) ABSTRACT

Biphenyl imidazoles and related compounds of Formula I, useful as antiviral agents, are provided herein. Pharmaceutical compositions containing a compound of Formula I, together with a second active agent, such as an NS3a protease inhibitor are provided herein. Methods for treating viral infections, including Hepatitis C infections, are included herein by providing a compound of Formula I together with an additional active agent. In certain embodiments the additional active agent is an NS3a protease inhibitor.

7 Claims, No Drawings

BIPHENYL IMIDAZOLES AND RELATED COMPOUNDS USEFUL FOR TREATING HCV INFECTIONS

PRIORITY INFORMATION

This application claims priority from U.S. Provisional Application No. 61/333,591 filed May 11, 2010, U.S. Provisional Application No. 61/352,137 filed Jun. 8, 2010, and U.S. Provisional Application 61/421,426 filed Dec. 9, 2010 all of which are hereby incorporated by reference in their entirety.

FIELD OF THE DISCLOSURE

The present disclosure provides biphenyl imidazoles and related compounds, useful as antiviral agents. Certain biphenyl imidazoles and related compounds disclosed herein are potent and/or selective inhibitors of viral replication, particularly Hepatitis C virus replication. Pharmaceutical compositions/and combinations containing one or more biphenyl imidazole or related compound and a pharmaceutically acceptable carrier are also provided by this disclosure. Particularly provided herein are pharmaceutical compositions or combinations containing a biphenyl imidazole or related compound together with an NS3a protease inhibitor such as a cyclized or linear 4-amino-4-oxobutanolyl peptide. Methods for treating viral infections, including Hepatitis C viral infections are provided by the disclosure.

BACKGROUND

An estimated 3% of the world's population is infected with the hepatitis C virus. Of those exposed to HCV, 80% to 85% become chronically infected, at least 30% develop cirrhosis of the liver and 1-4% develop hepatocellular carcinoma. Hepatitis C Virus (HCV) is one of the most prevalent causes of chronic liver disease in the United States, reportedly accounting for about 15 percent of acute viral hepatitis, 60 to 70 percent of chronic hepatitis, and up to 50 percent of cirrhosis, end-stage liver disease, and liver cancer. Chronic HCV infection is the most common cause of liver transplantation in the U.S., Australia, and most of Europe. Hepatitis C causes an estimated 10,000 to 12,000 deaths annually in the United States. While the acute phase of HCV infection is usually associated with mild symptoms, some evidence suggests that only about 15% to 20% of infected people will spontaneously clear HCV.

HCV is an enveloped, single-stranded RNA virus that contains a positive-stranded genome of about 9.6 kb. HCV is classified as a member of the Hepacivirus genus of the family Flaviviridae. At least 4 strains of HCV, GT-1-GT-4, have been characterized.

The HCV lifecycle includes entry into host cells; translation of the HCV genome, polyprotein processing, and replicase complex assembly; RNA replication, and virion assembly and release. Translation of the HCV RNA genome yields a more than 3000 amino acid long polyprotein that is processed by at least two cellular and two viral proteases. The HCV polyprotein is:

NH2-C-E1-E2-p7-NS2-NS3-NS4A-NS4B-NS5A-NS5B-COOH.

The cellular signal peptidase and signal peptide peptidase have been reported to be responsible for cleavage of the N-terminal third of the polyprotein (C-E1-E2-p7) from the nonstructural proteins (NS2-NS3-NS4A-NS4B-NS5A-NS5B). The NS2-NS3 protease mediates a first cis cleavage at the NS2-NS3 site. The NS3-NS4A protease then mediates a second cis-cleavage at the NS3-NS4A junction. The NS3-NS4A complex then cleaves at three downstream sites to separate the remaining nonstructural proteins. Accurate processing of the polyprotein is asserted to be essential for forming an active HCV replicase complex.

Once the polyprotein has been cleaved, the replicase complex comprising at least the NS3-NS5B nonstructural proteins assembles. The replicase complex is cytoplasmic and membrane-associated. Major enzymatic activities in the replicase complex include serine protease activity and NTPase helicase activity in NS3, and RNA-dependent RNA polymerase activity of NS5B. In the RNA replication process, a complementary negative strand copy of the genomic RNA is produced. The negative strand copy is used as a template to synthesize additional positive strand genomic RNAs that may participate in translation, replication, packaging, or any combination thereof to produce progeny virus. Assembly of a functional replicase complex has been described as a component of the HCV replication mechanism. U.S. Provisional Application No. 60/669,872 "Pharmaceutical Compositions and Methods of Inhibiting HCV Replication" filed Apr. 11, 2005, is hereby incorporated by reference in its entirety for its disclosure related to assembly of the replicase complex.

Current treatment of hepatitis C infection typically includes administration of an interferon, such as pegylated interferon (IFN), in combination with ribavirin. The success of current therapies as measured by sustained virologic response (SVR) depends on the strain of HCV with which the patient is infected and the patient's adherence to the treatment regimen. Only 50% of patients infected with HCV strain GT-1 exhibit a sustained virological response. Direct acting antiviral agents such as ACH-1625, VX-950 and NM 283 (prodrug of NM 107) are in clinical development for treatment of chronic HCV. Due to lack of effective therapies for treatment for certain HCV strains and the high mutation rate of HCV, new therapies are needed. The present invention fulfills this need and provides additional advantages, which are described herein.

SUMMARY

Biphenyl imidazoles and related compounds of Formula I are provided herein. The compounds of Formula I provided here posses antiviral activity.

The disclosure provides compounds of Formula I that are potent and/or selective inhibitors of Hepatitis C virus replication. Without being bound to any particular theory it is believed the present compounds are potent and selective inhibitors of HCV NS5A. Pharmaceutical compositions containing one or more compounds of Formula I, or a salt of such compounds, and one or more pharmaceutically acceptable carriers are also provided herein. Pharmaceutical combinations containing one or more compounds of Formula I, or a salt of such compounds, at least one additional active agent, and one or more pharmaceutically acceptable carriers are also provided herein.

Also disclosed are methods of treating patients suffering from certain infectious diseases by providing to such patients an amount of a compound of Formula I effective to reduce signs or symptoms of the disease or disorder. These infectious diseases include viral infections, particularly HCV infections. Methods of treatment include providing a compound of Formula I as a single active agent or providing a compound of Formula I in combination with one or more other therapeutic active agents.

In a first aspect the disclosure includes compounds of Formula I and pharmaceutically acceptable salts thereof:

Formula I

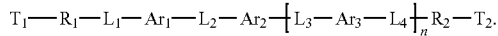

Within Formula I the variables $T_1$, $T_2$, $R_1$, $R_2$, $L_1$, $L_2$, $Ar_1$-$Ar_3$, and n carry the following definitions.

$T_1$ is $C_2$-$C_6$alkanoyl, $C_2$-$C_6$alkanoyl substituted with mono- or di-$C_1$-$C_6$alkylcarbamate, $C_2$-$C_6$alkanoyl substituted with mono- or di-$C_1$-$C_6$alkylcarboxamide, $C_1$-$C_6$alkylester, $C_1$-$C_6$alkylsulfonamide, or $C_1$-$C_6$alkylsulfonyl; each of which is optionally substituted with 1 or more substituents independently chosen from amino, cyano, hydroxyl, halogen, mono- and di-$C_1$-$C_4$alkylamino, $C_3$-$C_7$cycloalkyl, $C_1$-$C_4$alkoxy, $C_1$-$C_2$haloalkyl, $C_1$-$C_2$haloalkoxy, aryl, aryloxy, heteroaryl, or heteroaryloxy.

$R_1$ and $R_2$ are independently chosen from 5- to 6-membered rings containing one or two nitrogen atoms with remaining ring atoms being carbon, which $R_1$ and $R_2$ are saturated or contain 1 unsaturated bond and are optionally bridged with an methylene or ethylene bridge, or fused to a phenyl or 5- to 6-membered heteroaryl ring; and 9- to 10-membered fused bicyclic ring systems containing one or two nitrogen atoms with remaining ring atoms being carbon, which 9- to 10-membered bicyclic ring is saturated or contain 1 unsaturated bond. Each $R_1$ and $R_2$ is optionally substituted with one or more substituents independently chosen from cyano, halogen, $C_1$-$C_2$alkyl, and $C_1$-$C_2$alkoxy.

$L_1$ is a covalent bond or a $C_1$-$C_4$ alkylene group.

$Ar_1$ is a phenyl, pyridyl, pyrimidinyl, thiazolyl, oxazolyl, imidazolyl, indolinyl, or pyrrolidinyl group.

When $Ar_1$ is indolinyl, $R_1$ is absent.

When $T_1$ is substituted with $C_3$-$C_7$cycloalkyl, $R_1$ may be absent.

When $T_2$ is substituted with $C_3$-$C_7$cycloalkyl, $R_2$ may be absent;

$L_2$ is —NH(C=O)—, —(C=O)NH—, or a covalent bond.

$Ar_2$ is a group chosen from

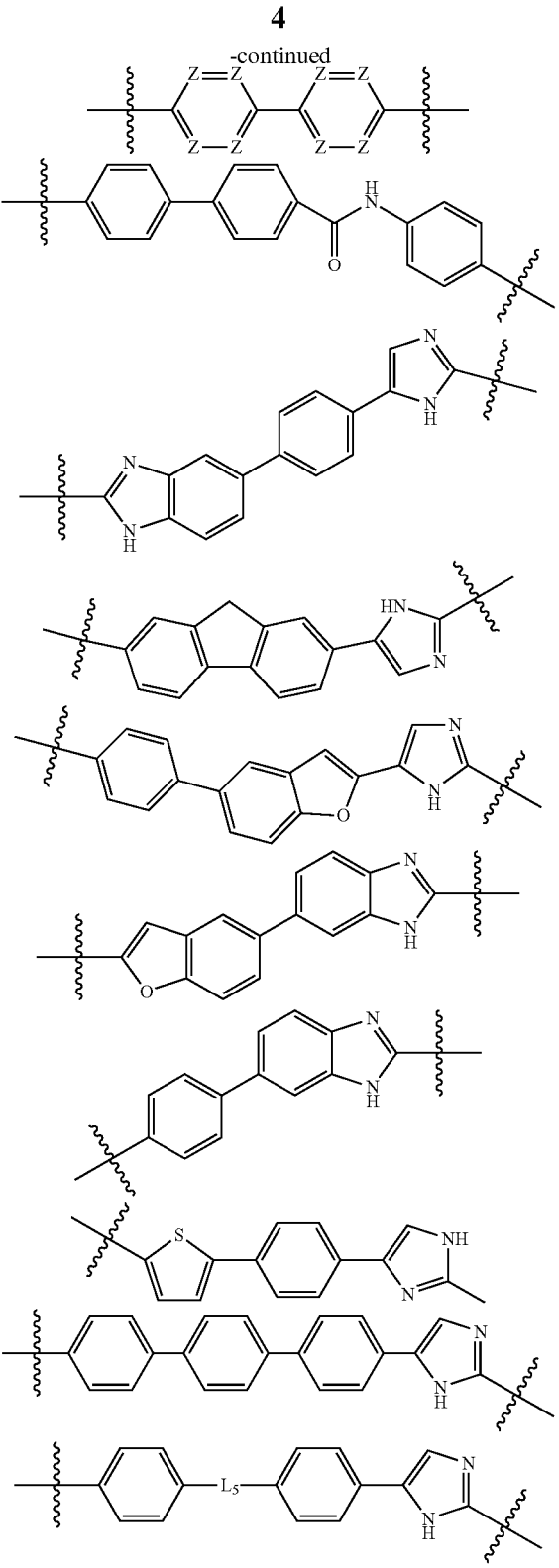

Z is independently chosen from CH and N, and no more than three Z in any ring are nitrogen; and n is 1 or 0.

$L_3$ is —NH(C=O)—, —(C=O)NH—, or a covalent bond.

$Ar_3$ is a phenyl or biphenyl group.

Each of $Ar_1$, $Ar_2$, and $Ar_3$ is optionally substituted with one or more substituents independently chosen from amino, cyano, hydroxyl, halogen, $C_1$-$C_4$alkyl, $C_1$-$C_4$alkoxy, mono- and di-$C_1$-$C_4$alkylamino, $C_1$-$C_2$haloalkyl, and $C_1$-$C_2$haloalkoxy;

$L_4$ is a covalent bond or a $C_1$-$C_4$ alkylene group.

$L_5$ is —O— or $C_2$-$C_4$alkenylene.

$T_2$ is absent or $T_2$ is a $C_2$-$C_6$alkanoyl, $C_2$-$C_6$alkanoyl substituted with $C_1$-$C_6$alkylcarbamate, $C_2$-$C_6$alkanoyl substituted with mono- or di-$C_1$-$C_6$alkylcarboxamide, $C_1$-$C_6$alkylester, $C_1$-$C_6$alkylsulfonyl, or $C_1$-$C_6$alkylsulfonamide; each of which is optionally substituted with 1 or more substituents independently chosen from amino, cyano, hydroxyl, halogen, mono- and di-$C_1$-$C_4$alkylamino, $C_1$-$C_4$alkoxy, $C_3$-$C_7$cycloalkyl, $C_1$-$C_2$haloalkyl, and $C_1$-$C_2$haloalkoxy.

Pharmaceutical compositions or combinations containing a compound of Formula I, which is believed to act as an HCV NS5a inhibitor together with a second active agent, believed to act as an HCV NS3a protease inhibitor are also provided by this disclosure. In certain embodiments the ND3a inhibitor is a compound of Formula II or a pharmaceutically acceptable salt thereof.

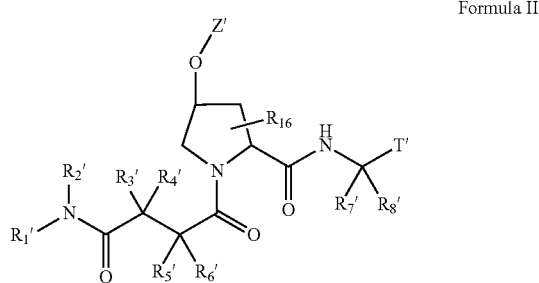

Formula II

Within Formula II the variables $R_1'$, $R_2'$, $R_3'$, $R_4'$, $R_6'$, $R_7'$, $R_8'$, $R_{16}$, and T' carry the definitions set forth below.

$R_1'$ and $R_2'$; are joined to form a 5- to 7-membered heterocycloalkyl ring containing 1 or 2 heteroatoms independently chosen from N, O, and S which ring is optionally fused to a phenyl or 5- or 6-membered heteroaryl to form a bicyclic ring system, each of which 5- to 7-membered heterocycloalkyl ring or bicyclic ring system is optionally substituted.

For the variables $R_3'$-$R_8'$ one of the following conditions is met.

$R_3'$, $R_4'$, $R_5'$, and $R_6'$ are independently hydrogen, $C_1$-$C_4$alkyl, or ($C_3$-$C_7$cycloalkyl)$C_0$-$C_4$alkyl; and $R_7'$ and $R_8'$ are joined to form an optionally substituted 3- to 7-membered cycloalkyl ring.

$R_3'$, $R_1'$, and $R_6'$ are independently hydrogen, $C_1$-$C_4$alkyl, or ($C_3$-$C_7$cycloalkyl)$C_0$-$C_4$alkyl; and $R_8'$ is hydrogen or $C_1$-$C_4$alkyl; and $R_5'$ is joined to $R_7'$ by a $C_0$-$C_{10}$ saturated or unsaturated hydrocarbon chain.

$R_3'$, $R_4'$, and $R_6'$ are independently hydrogen, $C_1$-$C_4$alkyl, or ($C_3$-$C_7$cycloalkyl)$C_0$-$C_4$alkyl; and $R_7'$ and $R_8'$ are joined to form an optionally substituted 3- to 7-membered cycloalkyl ring; and $R_5'$ is joined to the 3- to 7-membered optionally substituted cycloalkyl ring formed by $R_7$ and $R_8$ by a $C_6$-$C_{10}$ saturated or unsaturated hydrocarbon chain.

T' is a group of the formula:

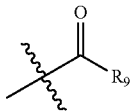

$R_9'$ is hydroxyl, amino, —COOH, —$NR_{10}R_{11}$, —$OR_{12}$, —$SR_{12}$, —$NR_{10}(S=O)R_{11}$, or —$NR_{10}SO_2R_{11}$. $R_{10}$, $R_{11}$, and $R_{12}$ are independently at each occurrence hydrogen, or $C_1$-$C_6$alkyl, $C_2$-$C_6$alkenyl, (aryl)$C_0$-$C_2$alkyl, ($C_3$-$C_7$cycloalkyl)$C_0$-$C_2$alkyl (heterocycloalkyl)$C_0$-$C_2$alkyl, or (5- to 10-membered heteroaryl)$C_0$-$C_2$alkyl, each of which is optionally substituted with 1 to 3 substituents independently chosen from halogen, hydroxyl, oxo, $C_1$-$C_2$alkyl, $C_1$-$C_2$alkoxy, trifluoromethyl, and trifluoromethoxy:

Z' is

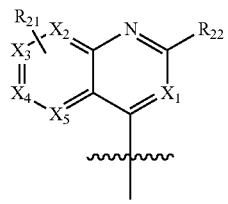

where $X_1$, $X_2$, $X_3$, $X_4$, and $X_5$ are independently N or CH and no more than two of $X_1$-$X_5$ are N.

$R_{21}$ represents from 0 to 3 groups independently chosen from halogen, hydroxyl, amino, cyano, —$CONH_2$, —COOH, $C_1$-$C_4$alkyl, $C_2$-$C_4$alkanoyl, $C_1$-$C_4$alkoxy, $C_1$-$C_4$alkylthio, mono- and di-$C_1$-$C_4$alkylamino, $C_1$-$C_2$haloalkyl, and $C_1$-$C_2$haloalkoxy.

$R_{22}$ is hydrogen, halogen, hydroxyl, amino, cyano, —$CONH_2$, —COOH, $C_1$-$C_4$alkyl, $C_2$-$C_4$alkanoyl, $C_1$-$C_4$alkoxy, $C_1$-$C_4$alkylthio, mono- and di-$C_1$-$C_4$alkylamino, $C_1$-$C_4$alkylester, $C_1$-$C_2$haloalkyl, and $C_1$-$C_2$haloalkoxy; or $R_{22}$ is ($C_3$-$C_7$cycloalkyl)$C_0$-$C_2$alkyl, (phenyl)$C_0$-$C_2$alkyl, (phenyl)$C_0$-$C_2$alkoxy, (5- or 6-membered heteroaryl)$C_0$-$C_2$alkyl, (5- or 6-membered heteroaryl)$C_0$-$C_2$alkoxy, naphthyl, indanyl, (5- or 6-membered heterocycloalkyl)$C_0$-$C_2$alkyl, or 9- or 10 membered bicyclic heteroaryl, each of which is substituted with 0, 1, or 2 substituents independently chosen from (i) halogen, hydroxyl, amino, cyano, nitro, —COOH, —$CONH_2$, $CH_3(C=O)NH$—, $C_1$-$C_4$alkyl, $C_1$-$C_4$alkoxy, $C_1$-$C_4$hydroxyalkyl, mono- and di-$C_1$-$C_4$alkylamino, —$NR_8SO_2R_{11}$, —$C(O)OR_{11}$, —$NR_8COR_{11}$, —$NR_8C(O)OR_{11}$, trifluoromethyl, trifluoromethoxy, and (ii) phenyl and 5- or 6-membered heteroaryl, each of which is substituted with 0 or 1 or more of halogen, hydroxyl, $C_1$-$C_4$alkyl, and $C_1$-$C_2$alkoxy.

$R_{16}$ represents 0 to 4 substituents is independently chosen at from halogen, $C_1$-$C_2$alkyl, and $C_1$-$C_2$alkoxy.

Certain compounds of Formula I disclosed herein exhibit good activity in an HCV replication assay, such as the HCV replicon assay set forth in Example 6, which follows. Preferred compounds of Formula I exhibit an $EC_{50}$ of about 10 micromolar or less, or more preferably an $EC_{50}$ of about 1 micromolar or less; or still more preferably an $EC_{50}$ of about 5 nanomolar or less in an HCV replicon replication assay

DETAILED DESCRIPTION

Chemical Description and Terminology

Prior to setting forth the invention in detail, it may be helpful to provide definitions of certain terms to be used herein. Presently disclosed compounds are described using standard nomenclature. Unless defined otherwise, all technical and scientific terms used herein have the same meaning as is commonly understood by one of skill in the art to which this invention belongs. Unless clearly contraindicated by the context each compound name includes the free acid or free base form of the compound as well hydrates of the compound and all pharmaceutically acceptable salts of the compound.

The term "compounds of Formula I" encompasses all compounds that satisfy Formula I, including any enantiomers, racemates and stereoisomers, as well as all pharmaceutically acceptable salts of such compounds. The phrase "a compound of Formula I" includes all subgeneric groups of Formula I, and also includes pharmaceutically acceptable salts of a compound of Formula I, unless clearly contraindicated by the context in which this phrase is used. In this disclosure Formula III is a subgeneric formula of Formula I.

"Formula II" encompasses all compounds that satisfy Formula II, including any enantiomers, racemates and stereoisomers, as well as all pharmaceutically acceptable salts of such compounds. The phrase "a compound of Formula II" includes all subgeneric groups of Formula II, and also includes pharmaceutically acceptable salts of a compound of Formula II, unless clearly contraindicated by the context in which this phrase is used.

The terms "a" and "an" do not denote a limitation of quantity, but rather denote the presence of at least one of the referenced item. The term "or" means "and/or". The terms "comprising", "having", "including", and "containing" are to be construed as open-ended terms (i.e., meaning "including, but not limited to"). Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art to which this invention belongs.

An "active agent" means a compound (including a compound disclosed herein), element, or mixture that when administered to a patient, alone or in combination with another compound, element, or mixture, confers, directly or indirectly, a physiological effect on the patient. The indirect physiological effect may occur via a metabolite or other indirect mechanism.

A dash ("-") that is not between two letters or symbols is used to indicate a point of attachment for a substituent. For example, —(C=O)NH$_2$ is attached through carbon of the keto (C=O) group.

"Alkanoyl" indicates an alkyl group as defined herein, attached through a keto (—(C=O)—) bridge. Alkanoyl groups have the indicated number of carbon atoms, with the carbon of the keto group being included in the numbered carbon atoms. For example a C$_2$alkanoyl group is an acetyl group having the formula CH$_3$(C=O)—.

A bond represented by a combination of a solid and dashed line, ie. =====, may be either a single or double bond.

"Alkyl" is a branched or straight chain saturated aliphatic hydrocarbon group, having the specified number of carbon atoms, generally from 1 to about 12 carbon atoms. The term C$_1$-C$_6$alkyl as used herein indicates an alkyl group having from 1, 2, 3, 4, 5, or 6 carbon atoms. Other embodiments include alkyl groups having from 1 to 8 carbon atoms, 1 to 4 carbon atoms or 1 or 2 carbon atoms, e.g. C$_1$-C$_8$alkyl, C$_1$-C$_4$alkyl, and C$_1$-C$_2$alkyl. When C$_0$-C$_n$ alkyl is used herein in conjunction with another group, for example, (aryl)C$_0$-C$_4$alkyl, the indicated group, in this case aryl, is either directly bound by a single covalent bond (C$_0$), or attached by an alkyl chain having the specified number of carbon atoms, in this case 1, 2, 3, or 4 carbon atoms. C$_0$-C$_n$alkyl is used in conjunction with heteroaryl, aryl, phenyl, cycloalkyl, and heterocycloalkyl, e.g., (5- to 10-membered heteroaryl)C$_0$-C$_2$alkyl, (aryl)C$_0$-C$_2$alkyl, (phenyl)C$_0$-C$_2$alkyl, (C$_3$-C$_7$cycloalkyl)C$_0$-C$_4$alkyl, and (heterocycloalkyl)C$_0$-C$_4$alkyl. Examples of alkyl include, but are not limited to, methyl, ethyl, n-propyl, isopropyl, n-butyl, 3-methylbutyl, t-butyl, n-pentyl, and sec-pentyl.

"Alkylene" is a saturated organic radical of the formula —(CH$_2$)$_n$— where n is the number of CH$_2$ groups in the alkylene radical. Alkylene radicals having from 1 to 6 carbons or from 1 to 4 carbons are usually preferred.

"Alkoxy" indicates an alkyl group as defined above with the indicated number of carbon atoms attached through an oxygen bridge (—O—). Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy. When "C$_0$-C$_0$alkoxy" is used in with another group, for example, (heteroaryl)C$_0$-C$_4$ alkoxy, the indicated group, in this case heteroaryl, is either attached via a covalently bound oxygen bridge (C$_0$alkoxy), or attached by an alkoxy group having the specified number of carbon atoms, in this case from 1 to about 4 carbon atoms, that is covalently bound to the group it substitutes via the alkoxy oxygen atom.

The term "alkylester" indicates an alkyl group as defined herein attached through an ester linkage. The ester linkage may be in either orientation, e.g. a group of the formula —O(C=O)alkyl or a group of the formula —(C=O)Oalkyl.

"Alkylsulfonyl" is a group of the formula —SO$_2$alkyl, where the alkyl group carries the definition set forth herein.

"Aryl" indicates an aromatic group containing only carbon in the aromatic ring or rings. Such aromatic groups may be further substituted with carbon or non-carbon atoms or groups. Typical aryl groups contain 1 or 2 separate, fused, or pendant rings and from 6 to about 12 ring atoms, without heteroatoms as ring members. Where indicated aryl groups may be substituted. Such substitution may include fusion to a 5 to 7-membered saturated cyclic group that optionally contains 1 or 2 heteroatoms independently chosen from N, O, and S, to form, for example, a 3,4-methylenedioxy-phenyl group. Aryl groups include, for example, phenyl, naphthyl, including 1-naphthyl and 2-naphthyl, and bi-phenyl. An "aryloxy" group is an aryl group as described herein bound to the group it substitutes via an oxygen bridge.

"Haloalkyl" indicates both branched and straight-chain alkyl groups having the specified number of carbon atoms, substituted with 1 or more halogen atoms, up to the maximum allowable number of halogen atoms. Examples of haloalkyl include, but are not limited to, trifluoromethyl, difluoromethyl, 2-fluoroethyl, and penta-fluoroethyl.

"Haloalkoxy" indicates a haloalkyl group as defined herein attached through an oxygen bridge (oxygen of an alcohol radical).

"Halo" or "halogen" indicates any of fluoro, chloro, bromo, and iodo.

"Heteroaryl" indicates a stable monocyclic aromatic ring having the indicated number of ring atoms which contains from 1 to 3, or in some embodiments from 1 to 2, heteroatoms chosen from N, O, and S, with remaining ring atoms being carbon, or a stable bicyclic or tricyclic system containing at least one 5- to 7-membered aromatic ring which contains from 1 to 3, or in some embodiments from 1 to 2, heteroatoms chosen from N, O, and S, with remaining ring atoms being carbon. Monocyclic heteroaryl groups typically have from 5 to 7 ring atoms. In some embodiments bicyclic heteroaryl groups are 9- to 10-membered heteroaryl groups, that is, groups containing 9 or 10 ring atoms in which one 5- to 7-member aromatic ring is fused to a second aromatic or non-aromatic ring. When the total number of S and O atoms in the heteroaryl group exceeds 1, these heteroatoms are not adjacent to one another. It is preferred that the total number of S and O atoms in the heteroaryl group is not more than 2. It is particularly preferred that the total number of S and O atoms in the aromatic heterocycle is not more than 1. Examples of heteroaryl groups include, but are not limited to, oxazolyl, pyranyl, pyrazinyl, pyrazolopyrimidinyl, pyrazolyl, pyridizinyl, pyridyl, pyrimidinyl, pyrrolyl, quinolinyl, tetrazolyl, thiazolyl, thienylpyrazolyl, thiophenyl, triazolyl, benzo[d]oxazolyl, benzofuranyl, benzothiazolyl, benzothiophenyl, benzoxadiazolyl, dihydrobenzodioxynyl, furanyl, imidazolyl, indolyl, and isoxazolyl. "Heteroaryloxy" is a heteroaryl group as described bound to the group it substituted via an oxygen bridge.

The term "mono- and/or di-alkylamino" indicates secondary or tertiary alkyl amino groups, wherein the alkyl groups are independently chosen alkyl groups, as defined herein, having the indicated number of carbon atoms. The point of attachment of the alkylamino group is on the nitrogen. Examples of mono- and di-alkylamino groups include ethylamino, dimethylamino, and methyl-propyl-amino.

"Mono- and/or di-alkylcarboxamide" indicates a monoalkylcarboxamide group of formula $(alkyl_1)$—NH—(C=O)— or a dialkylcarboxamide group of the formula $(alkyl_1)(alkyl_2)$—N—(C=O)— in which the point of attachment of the mono- or dialkylcarboxamide substituent to the molecule it substitutes is on the carbon of the carbonyl group. The term "mono and/or dialkylcarboxamide" also includes groups of the formula $(alkyl_1)(C=O)NH$— and $(alkyl_1)(C=O) (alkyl_2)N$— in which the point of attachment is the nitrogen atom. The groups $alkyl_1$ and $alkyl_2$ are independently chosen alkyl groups having the indicated number of carbon atoms.

The term "substituted", as used herein, means that any one or more hydrogens on the designated atom or group is replaced with a selection from the indicated group, provided that the designated atom's normal valence is not exceeded. When the substituent is oxo (i.e., =O) then 2 hydrogens on the atom are replaced. When an oxo group substitutes aromatic moieties, the corresponding partially unsaturated ring replaces the aromatic ring. For example a pyridyl group substituted by oxo is a pyridone. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation into an effective therapeutic agent. Unless otherwise specified substituents are named into the core structure. For example, it is to be understood that when aminoalkyl is listed as a possible substituent the point of attachment of this substituent to the core structure is in the alkyl portion.

Suitable groups that may be present on a "substituted" position include, but are not limited to, e.g., halogen; cyano; hydroxyl; nitro; azido; alkanoyl (such as a $C_2$-$C_6$ alkanoyl group such as acyl or the like); carboxamido; alkyl groups (including cycloalkyl groups) having 1 to about 8 carbon atoms, or 1 to about 6 carbon atoms; alkenyl and alkynyl groups including groups having one or more unsaturated linkages and from 2 to about 8, or 2 to about 6 carbon atoms; alkoxy groups having one or more oxygen linkages and from 1 to about 8, or from 1 to about 6 carbon atoms; aryloxy such as phenoxy; alkylthio groups including those having one or more thioether linkages and from 1 to about 8 carbon atoms, or from 1 to about 6 carbon atoms; alkylsulfinyl groups including those having one or more sulfinyl linkages and from 1 to about 8 carbon atoms, or from 1 to about 6 carbon atoms; alkylsulfonyl groups including those having one or more sulfonyl linkages and from 1 to about 8 carbon atoms, or from 1 to about 6 carbon atoms; aminoalkyl groups including groups having one or more N atoms and from 1 to about 8, or from 1 to about 6 carbon atoms; aryl having 6 or more carbons and one or more rings, (e.g., phenyl, biphenyl, naphthyl, or the like, each ring either substituted or unsubstituted aromatic); arylalkyl having 1 to 3 separate or fused rings and from 6 to about 18 ring carbon atoms, with benzyl being an exemplary arylalkyl group; arylalkoxy having 1 to 3 separate or fused rings and from 6 to about 18 ring carbon atoms, with benzyloxy being an exemplary arylalkoxy group; or a saturated, unsaturated, or aromatic heterocyclic group having 1 to 3 separate or fused rings with 3 to about 8 members per ring and one or more N, O or S atoms, e.g. coumarinyl, quinolinyl, isoquinolinyl, quinazolinyl, pyridyl, pyrazinyl, pyrimidinyl, furanyl, pyrrolyl, thienyl, thiazolyl, triazinyl, oxazolyl, isoxazolyl, imidazolyl, indolyl, benzofuranyl, benzothiazolyl, tetrahydrofuranyl, tetrahydropyranyl, piperidinyl, morpholinyl, piperazinyl, and pyrrolidinyl. Such heterocyclic groups may be further substituted, e.g. with hydroxy, alkyl, alkoxy, halogen and amino.

A "dosage form" means a unit of administration of an active agent. Examples of dosage forms include tablets, capsules, injections, suspensions, liquids, emulsions, creams, ointments, suppositories, inhalable forms, transdermal forms, and the like.

"Pharmaceutical compositions" are compositions comprising at least one active agent, such as a compound or salt of Formula I, and at least one other substance, such as a carrier. Pharmaceutical compositions meet the U.S. FDA's GMP (good manufacturing practice) standards for human or non-human drugs. "Pharmaceutical combinations" are combinations of at least two active agents which may be combined in a single dosage form or provided together in separate dosage forms with instructions that the active agents are to be used together to treat a disorder, such as hepatitis C.

"Pharmaceutically acceptable salts" includes derivatives of the disclosed compounds in which the parent compound is modified by making inorganic and organic, non-toxic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, $HOOC-(CH_2)_n-COOH$ where n is 0-4, and the like. Lists of additional suitable salts may be found, e.g., in *Remington's Pharmaceutical Sciences,* 17th ed., Mack Publishing Company, Easton, Pa., p. 1418 (1985).

The term "carrier" applied to pharmaceutical compositions/combinations of the invention refers to a diluent, excipient, or vehicle with which an active compound is provided.

A "pharmaceutically acceptable excipient" means an excipient that is useful in preparing a pharmaceutical composition/combination that is generally safe, non-toxic and neither biologically nor otherwise undesirable, and includes an excipient that is acceptable for veterinary use as well as human pharmaceutical use. A "pharmaceutically acceptable excipient" as used in the present application includes both one and more than one such excipient.

A "patient" is a human or non-human animal in need of medical treatment. Medical treatment can include treatment of an existing condition, such as a disease or disorder, prophylactic or preventative treatment, or diagnostic treatment. In some embodiments the patient is a human patient.

"Providing" means giving, administering, selling, distributing, transferring (for profit or not), manufacturing, compounding, or dispensing.

"Providing a compound of Formula I with at least one additional active agent" means the compound of Formula I and the additional active agent(s) are provided simultaneously in a single dosage form, provided concomitantly in separate dosage forms, or provided in separate dosage forms for administration separated by some amount of time that is within the time in which both the compound of Formula I and the at least one additional active agent are within the blood stream of a patient. The compound of Formula I and the additional active agent need not be prescribed for a patient by the same medical care worker. The additional active agent or agents need not require a prescription. Administration of the compound of Formula I or the at least one additional active agent can occur via any appropriate route, for example, oral tablets, oral capsules, oral liquids, inhalation, injection, suppositories or topical contact.

"Treatment," as used herein includes providing a compound of Formula I, either as the only active agent or together with at least one additional active agent sufficient to: (a) prevent a disease or a symptom of a disease from occurring in a patient who may be predisposed to the disease but has not yet been diagnosed as having it (e.g. including diseases that may be associated with or caused by a primary disease (as in liver fibrosis that can result in the context of chronic HCV infection); (b) inhibiting the disease, i.e. arresting its development; and (c) relieving the disease, i.e., causing regression of the disease. "Treating" and "treatment" also means providing a therapeutically effective amount of a compound of Formula I, as the only active agent or together with at least one additional active agent to a patient having or susceptible to a hepatitis C infection.

A "therapeutically effective amount" of a pharmaceutical composition/combination of this invention means an amount effective, when administered to a patient, to provide a therapeutic benefit such as an amelioration of symptoms, e.g., an amount effective to decrease the symptoms of a hepatitis C infection. For example a patient infected with a hepatitis C virus may present elevated levels of certain liver enzymes, including AST and ALT. Normal levels of AST are from 5 to 40 units per liter of serum (the liquid part of the blood) and normal levels of ALT are from 7 to 56 units per liter of serum. A therapeutically effect amount is thus an amount sufficient to provide a significant reduction in elevated AST and ALT levels or an amount sufficient to provide a return of AST and ALT levels to the normal range. A therapeutically effective amount is also an amount sufficient to prevent a significant increase or significantly reduce the detectable level of virus or viral antibodies in the patient's blood, serum, or tissues. One method of determining treatment efficacy includes measuring HCV RNA levels by a conventional method for determining viral RNA levels such as the Roch TaqMan assay. In certain preferred embodiments treatment reduces HCV RNA levels below the limit of quantitation (30 IU/mL, as measured by the Roche TaqMan(R) assay) or more preferably below the limit of detection (10 IU/mL, Roche TaqMan).

A significant increase or reduction in the detectable level of virus or viral antibodies is any detectable change that is statistically significant in a standard parametric test of statistical significance such as Student's T-test, where $p<0.05$.

Chemical Description

Formula I and Formula II include all subformulae thereof. In certain situations, the compounds of Formula I or Formula II may contain one or more asymmetric elements such as stereogenic centers, stereogenic axes and the like, e.g. asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, it should be understood that all of the optical isomers and mixtures thereof are encompassed. In addition, compounds with carbon-carbon double bonds may occur in Z- and E-forms, with all isomeric forms of the compounds being included in the present invention. In these situations, single enantiomers, i.e., optically active forms, can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example using a chiral HPLC column.

Where a compound exists in various tautomeric forms, the invention is not limited to any one of the specific tautomers, but rather includes all tautomeric forms.

The present invention is intended to include all isotopes of atoms occurring in the present compounds. Isotopes include those atoms having the same atomic number but different mass numbers. By way of general example, and without limitation, isotopes of hydrogen include tritium and deuterium and isotopes of carbon include $^{11}C$, $^{13}C$, and $^{14}C$.

Certain compounds are described herein using a general formula that includes variables, e.g. $T_1$, $T_2$, n, $L_1$, $L_2$, $R_1$, $R_2$, $Ar_1$-$Ar_3$, and Z. Unless otherwise specified, each variable within such a formula is defined independently of other variables. Thus, if a group is said to be substituted, e.g. with 0-2 R*, then the group may be substituted with up to two R* groups and R* at each occurrence is selected independently from the definition of R*. Also, combinations of substituents and/or variables are permissible only if such combinations result in stable compounds.

In addition the compounds and salts of Formula I discussed in the SUMMARY section, the disclosure includes compounds and salt of Formula I, and pharmaceutical compositions/combinations of such compounds in which the variables meet any of the following conditions.

Formula I

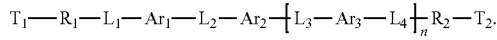

(i) n is 0; and $R_1$ and $R_2$ are independently chosen from 5- or 6-membered rings containing one or two nitrogen atoms with remaining ring atoms being carbon, which are saturated or contain 1 unsaturated bond and are optionally bridged with an methylene or ethylene bridge, or fused to a phenyl; each $R_1$ and $R_2$ is optionally substituted one or more substituents independently chosen from cyano, halogen, $C_1$-$C_2$alkyl, $C_1$-$C_2$alkoxy.

(ii) n is 0; $R_1$ and $R_2$ are independently chosen from piperazine, piperidine, 1-H-dihydropyrrole, pyrrolidine, indoline, azepane, methylene and ethylene bridged piperazine, and methylene and ethylene bridged piperidine groups; wherein each $R_1$ and $R_2$ is optionally substituted with one or more substituents independently chosen from halogen, $C_1$-$C_2$alkyl and $C_1$-$C_2$alkoxy; and

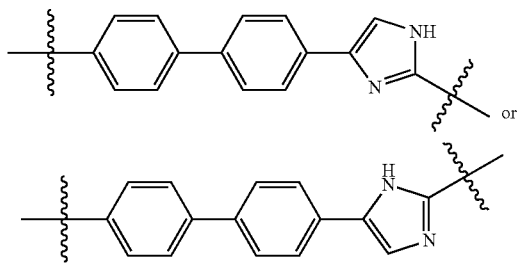

$Ar_2$ is $Ar_2$ is optionally substituted with one or more substituents independently chosen from halogen, $C_1$-$C_2$alkyl, and $C_1$-$C_2$alkoxy.

(iii) $L_1$ is a covalent bond; $Ar_1$ is an imidazolyl group; and $L_2$ is a covalent bond.

(iv) $R_1$ and $R_2$ are independently chosen from piperazine, piperidine, 1-H-dihydropyrrole, pyrrolidine, azepane, methylene and ethylene bridged piperazine, and methylene and ethylene bridged piperidine groups; wherein each $R_1$ and $R_2$ is optionally substituted with one or two substituents independently chosen from halogen, $C_1$-$C_2$alkyl and $C_1$-$C_2$alkoxy.

(v) $T_1$ and $T_2$ are independently selected from $C_1$-$C_6$alkylsulfonamide, $C_1$-$C_6$alkylsulfonyl, $C_2$-$C_6$alkanoyl substituted with mono- or di-$C_1$-$C_6$alkylcarbamate, and $C_2$-$C_6$alkanoyl substituted with mono- or di-$C_1$-$C_6$alkylcarboxamide.

In addition the compounds and salts of Formula II discussed in the SUMMARY section, the disclosure includes compositions and combinations of Formula II and Formula I, in which the variables in Formula II meet any of the following conditions.

Formula II

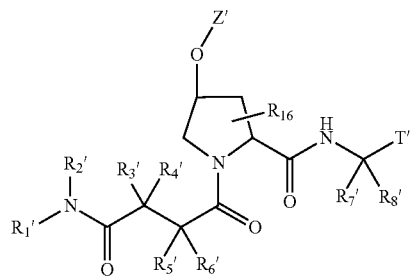

(i) $R_1'$ and $R_2'$ are joined to form a pyrrolidine, piperidine, or piperazine ring, a piperazine ring fused to a phenyl, or a piperidine ring fused to a phenyl, each of which is optionally substituted with 1 to 2 substituents independently chosen from halogen, hydroxyl, amino, $CONH_2$, —COOH, $C_1$-$C_2$alkyl, and $C_1$-$C_2$alkoxy; and $R_3'$ and $R_4'$ are hydrogen or methyl.

(ii) $R_5'$ is $C_1$-$C_4$alkyl, or ($C_3$-$C_7$cycloalkyl)$C_0$-$C_4$alkyl; and $R_6'$ and $R_8'$ are independently hydrogen or methyl; or $R_5'$ is joined to $R_7'$ by a $C_6$-$C_{10}$ saturated or mono-unsaturated hydrocarbon chain; and $R_6'$ and $R_8'$ are independently hydrogen or methyl; or $R_7'$ and $R_8'$ are joined to form an cyclopropyl ring; and $R_5'$ is joined to the cyclopropyl ring formed by $R_7$ and $R_8$ by a $C_6$-$C_{10}$ saturated or mono-unsaturated hydrocarbon chain, and $R_6'$ is hydrogen or methyl.

(iii) T' is a group of the formula

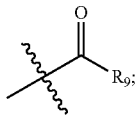

and $R_9$ is hydroxyl, —$OR_{12}$ or —$NR_{10}SO_2R_{11}$; $R_{10}$ is hydrogen or methyl; $R_{11}$ is $C_1$-$C_4$alkyl or cyclopropyl; and $R_{12}$ is $C_1$-$C_4$alkyl.

(iv) Z' is a quinoline of the formula

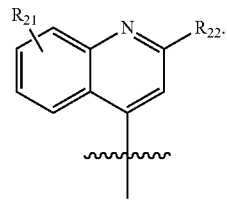

$R_{21}$ represents a substituent at the 7-position of the quinoline, and 0 to 2 additional substituents all of which are independently chosen from halogen, hydroxyl, amino, cyano, —$CONH_2$, —COOH, $C_1$-$C_4$alkyl, $C_2$-$C_4$alkanoyl, $C_1$-$C_4$alkoxy, mono- and di-$C_1$-$C_4$alkylamino, $C_1$-$C_2$haloalkyl, and $C_1$-$C_2$haloalkoxy; and $R_{22}$ is (phenyl)$C_0$-$C_2$alkyl, (pyridyl)$C_0$-$C_2$alkyl, or (thiazolyl)$C_0$-$C_2$alkyl, each of which is substituted with 0, 1, or 2 substituents independently chosen from halogen, hydroxyl, amino, cyano, —COOH, —$CONH_2$, $C_1$-$C_4$alkyl, $C_1$-$C_4$alkoxy, mono- and di-$C_1$-$C_4$alkylamino, trifluoromethyl, and trifluoromethoxy.

This disclosure also provides compounds and salts of Formula III and pharmaceutical compositions and combinations comprising a compound or salt of Formula III.

Formula III

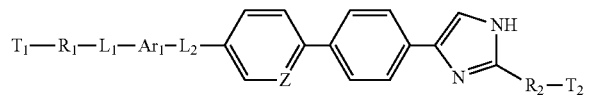

Within Formula III the variables carry the following definitions.

$T_1$ and $T_2$ are independently chosen from

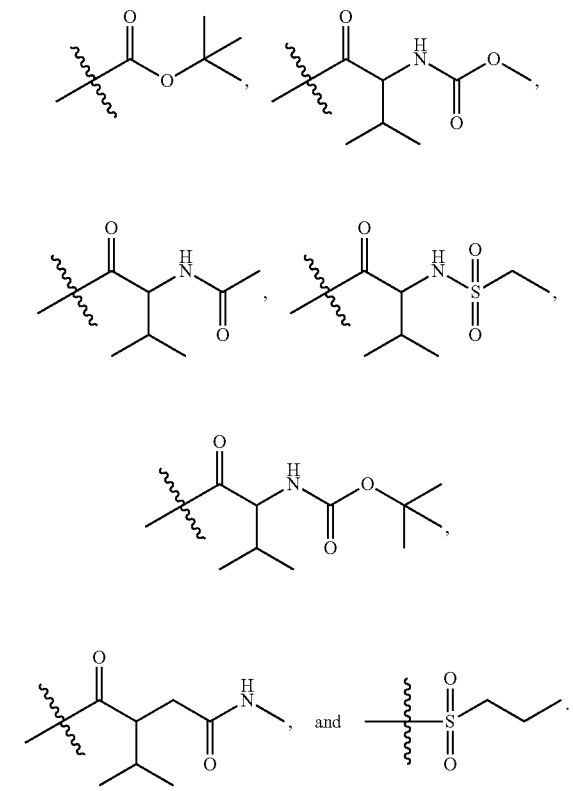

wherein $T_2$ may be absent.

$R_1$ and $R_2$ are independently chosen from 5- or 6-membered rings containing one or two nitrogen atoms with remaining ring atoms being carbon, which are is saturated or contain 1 unsaturated bond and are optionally bridged with an methylene or ethylene bridge, or fused to a phenyl ring; each $R_1$ and $R_2$ is optionally substituted with one or more substituents independently chosen from cyano, halogen, $C_1$-$C_2$alkyl, and $C_1$-$C_2$alkoxy.

One of $R_1$ and $R_2$ is not methylene bridged piperidine when the other of $R_1$ and $R_2$ is pyrrolidine.

$L_1$ and $L_2$ are independently a covalent bond, —NH(C=O)—, —(C=O)NH—, or a methylene group.

$Ar_1$ is

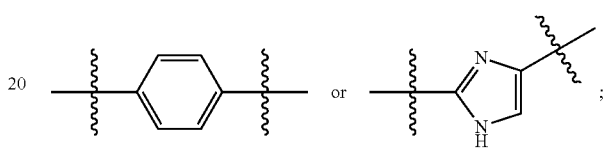

and

Z is chosen from CH and N.

The disclosure also includes compounds and salts of Formula III, and pharmaceutical compositions or combinations of Formula III in which any of the following conditions are met.

(i) $L_1$ is a covalent bond or a methylene group;

$L_2$ is —(C=O)NH— or —NH(C=O)—; and $R_1$ is piperazine; and $R_2$ is pyrrolidine.

(ii) $L_1$ is a covalent bond or a methylene group;

$L_2$ is a covalent bond; and $R_1$ and $R_2$ are independently chosen from piperidine, pyrrolidine, methylene and ethylene bridged piperazine, and methylene and ethylene bridged piperidine.

(iii) $L_1$ and $L_2$ are both a covalent bond; and $R_1$ and $R_2$ are both piperidine, 1-H dihydropyrrole, pyrrolidine, indoline, or a methylene or ethylene bridged piperidine.

(iv) $R_1$ and $R_2$ are independently chosen from piperazine, piperidine, 1-H dihydropyrrole, pyrrolidine, indoline, methylene and ethylene bridged piperazine, and methylene and ethylene bridged piperidine groups, wherein each $R_1$ and $R_2$ is optionally substituted with one or more substituents independently chosen from halogen, $C_1$-$C_2$alkyl and $C_1$-$C_2$alkoxy.

Any of the preceding conditions for compounds of Formula I, II, and III may be used together to define a subgeneric formula of Formula I, II, or III so long as a stable compound results and all such subgeneric formulas are included in this disclosure.

This disclosure also includes pharmaceutical compositions and combinations comprising a compound of Formula I and a compound of Formula II. As well as methods of treatment comprising administering such compositions/combinations to a patient infected with hepatitis C.

For example the disclosure includes compositions and combinations in which the compound of Formula I is

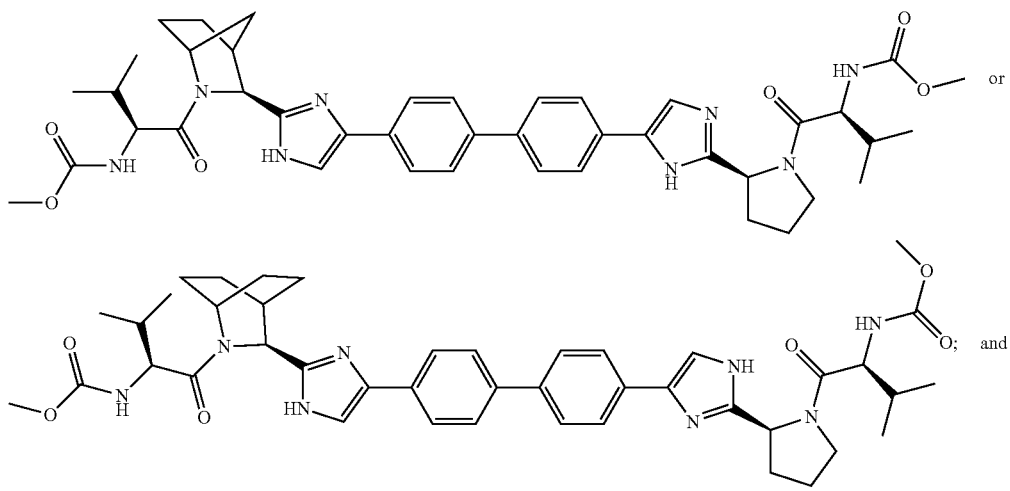

the compound of Formula II is

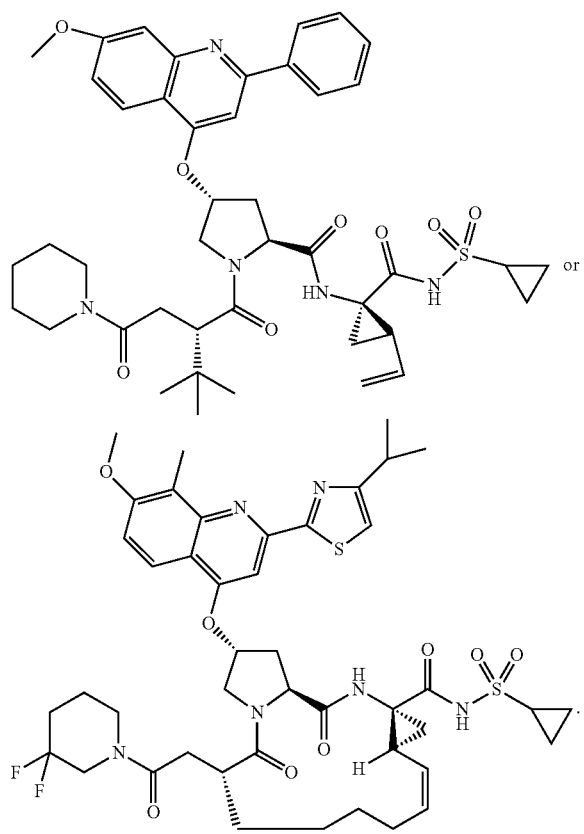

NS3a protease inhibitors of Formula II, useful in the pharmaceutical compositions and combinations described here have been disclosed previously. U.S. Pat. No. 7,906,619, issued Mar. 15, 2011, is hereby incorporated by reference in its entirety for its teachings regarding 4-amino-4-oxobutanoyl peptides. The '619 patent is particularly incorporated by reference at the Examples section beginning in column 50 and extending to column 85 which discloses compounds useful in compositions/combination with Compounds of Formula I described here.

Published US Pat. Appl. No. 2010-0216725, published Aug. 26, 2010, is hereby incorporated by reference in its entirety for its teachings regarding 4-amino-4-oxobutanoyl peptides. The '725 application is particularly incorporated by reference at the Examples section beginning at page 22 and extending to page 100 which discloses compounds useful in compositions/combination with Compounds of Formula I described here.

Published US Pat. Appl. No. 2010-0152103, published Jun. 17, 2010, is hereby incorporated by reference in its entirety for its teachings regarding 4-amino-4-oxobutanoyl peptide cyclic analogues. The '103 application is particularly incorporated by reference at the Examples section beginning at page 19 and extending to page 60 which discloses compounds useful in compositions/combination with Compounds of Formula I described here.

Pharmaceutical Preparations

Compounds disclosed herein can be administered as the neat chemical, but are preferably administered as a pharmaceutical composition. Accordingly, the disclosure provides pharmaceutical compositions comprising a compound or pharmaceutically acceptable salt of Formula I, together with at least one pharmaceutically acceptable carrier. The pharmaceutical composition/combination may contain a compound or salt of Formula I as the only active agent, but is preferably contains at least one additional active agent. In certain embodiments it is preferred that the additional active agent is an NS3a protease inhibitor, such as a compound of salt of Formula II. In certain embodiments the pharmaceutical composition is in a dosage form that contains from about 0.1 mg to about 2000 mg, from about 10 mg to about 1000 mg, from about 100 mg to about 800 mg, or from about 200 mg to about 600 mg of a compound of Formula I and optionally from about 0.1 mg to about 2000 mg, from about 10 mg to about 1000 mg, from about 100 mg to about 800 mg, or from about 200 mg to about 600 mg of an additional active agent in a unit dosage form. The pharmaceutical composition may also include a molar ratio of a compound of Formula I and an additional active agent. For example the pharmaceutical composition may contain a molar ratio of about 0.5:1, about 1:1, about 2:1, about 3:1 or from about 1.5:1 to about 4:1 of an NS3a protease inhibitor of Formula II to NS5a inhibitor of Formula I.

Compounds disclosed herein may be administered orally, topically, parenterally, by inhalation or spray, sublingually, transdermally, via buccal administration, rectally, as an ophthalmic solution, or by other means, in dosage unit formulations containing conventional pharmaceutically acceptable carriers. The pharmaceutical composition may be formulated as any pharmaceutically useful form, e.g., as an aerosol, a cream, a gel, a pill, a capsule, a tablet, a syrup, a transdermal patch, or an ophthalmic solution. Some dosage forms, such as tablets and capsules, are subdivided into suitably sized unit doses containing appropriate quantities of the active components, e.g., an effective amount to achieve the desired purpose.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound.

Classes of carriers include, but are not limited to binders, buffering agents, coloring agents, diluents, disintegrants, emulsifiers, flavorants, glidents, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin; talc, and vegetable oils. Optional active agents may be included in a pharmaceutical composition, which do not substantially interfere with the activity of the compound of the present invention.

The pharmaceutical compositions/combinations can be formulated for oral administration. These compositions contain between 0.1 and 99 weight % (wt. %) of a compound of Formula I and usually at least about 5 wt. % of a compound of Formula. Some embodiments contain from about 25 wt. % to about 50 wt. % or from about 5 wt. % to about 75 wt. % of the compound of Formula.

Methods of Treatment

The pharmaceutical compositions/combinations disclosed herein are useful for treating hepatitis C infections in patients.

This disclosure provides methods of treating viral infections, including hepatitis C infections, by providing an effective amount of a compound or pharmaceutically acceptable salt of Formula I to patient infected with a hepatitis C virus. A compound or salt of Formula I may be provided as the only active agent or may be provided together with one or more additional active agents. In certain embodiments the compound or salt of Formula I is administered together with a compound or salt of Formula II or other NS3a protease inhibitor. In certain embodiment the pharmaceutical composition contains a compound of Formula I together with an NS5b inhibitor, and optionally an additional active agent.

An effective amount of a pharmaceutical composition/combination of the invention may be an amount sufficient to (a) inhibit the progression of hepatitis C; (b) cause a regression of the hepatitis C infection; or (c) cause a cure of a hepatitis C infection such that HCV virus or HCV antibodies can no longer be detected in a previously infected patient's blood or plasma. An amount of a pharmaceutical composition/combination effective to inhibit the progress or cause a regression of hepatitis C includes an amount effective to stop the worsening of symptoms of hepatitis C or reduce the symptoms experienced by a patient infected with the hepatitis C virus. Alternatively a halt in progression or regression of hepatitis C may be indicated by any of several markers for the disease. For example, a lack of increase or reduction in the hepatitis C viral load or a lack of increase or reduction in the number of circulating HCV antibodies in a patient's blood are markers of a halt in progression or regression of hepatitis C infection. Other hepatitis C disease markers include aminotransferase levels, particularly levels of the liver enzymes AST and ALT. Normal levels of AST are from 5 to 40 units per liter of serum (the liquid part of the blood) and normal levels of ALT are from 7 to 56 units per liter of serum. These levels will typically be elevated in a HCV infected patient. Disease regression is usually marked by the return of AST and ALT levels to the normal range.

Symptoms of hepatitis C that may be affected by an effective amount of a pharmaceutical composition/combination of the invention include decreased liver function, fatigue, flu-like symptoms: fever, chills, muscle aches, joint pain, and headaches, nausea, aversion to certain foods, unexplained weight loss, psychological disorders including depression, tenderness in the abdomen, and jaundice.

"Liver function" refers to a normal function of the liver, including, but not limited to, a synthetic function including synthesis of proteins such as serum proteins (e.g., albumin, clotting factors, alkaline phosphatase, aminotransferases (e.g., alanine transaminase, aspartate transaminase), 5'-nucleosidase, y glutaminyltranspeptidase, etc.), synthesis of bilirubin, synthesis of cholesterol, and synthesis of bile acids; a liver metabolic function, including carbohydrate metabolism, amino acid and ammonia metabolism, hormone metabolism, and lipid metabolism; detoxification of exogenous drugs; and a hemodynamic function, including splanchnic and portal hemodynamics.

An effective amount of a pharmaceutical composition/combination described herein will also provide a sufficient concentration of the active agents in the concentration when administered to a patient. A sufficient concentration of an active agent is a concentration of the agent in the patient's body necessary to prevent or combat the infection. Such an amount may be ascertained experimentally, for example by assaying blood concentration of the agent, or theoretically, by calculating bioavailability. The amount of an active agent sufficient to inhibit viral infection in vitro may be determined with a conventional assay for viral infectivity such as a replicon based assay, which has been described in the literature.

Pharmaceutical compositions/combinations and methods of treatment in which a compound or salt of Formula I is provided together with one or more additional active agents are included herein. In preferred embodiments a compound of Formula I is provided together with an NS3a protease inhibitor, either in a single pharmaceutical composition or a in separate dosage forms with instructions to the patient to use the compound of Formula I and additional active agent together. Compounds of Formula II and compounds disclosed in U.S. Pat. No. 7,906,619, US Pat. Appl. No. 2010-0216725, and US Pat. Appl. No. 2010-0152103, most of which are within the scope of Formula II, are suitable NS3a protease inhibitors for use in combination with compounds and salts of Formula I. In certain embodiments the active agent (or agents) is an HCV protease inhibitor or HCV polymerase inhibitor. For example the protease inhibitor may be telaprevir (VX-950) and the polymerase inhibitor may be valopicitabine, or NM 107, the active agent which valopicitabine is converted into in vivo. In certain embodiments the at least one additional active agent is ribavirin, interferon, or Peg-interferon alpha conjugate. In certain embodiments the at least one additional active agent is ACH-1625 or ACH-2684.

According to the methods of the invention, the compound or pharmaceutically acceptable salt of Formula I and at least one additional active agent may be: (1) co-formulated and administered or delivered simultaneously in a combined formulation; (2) delivered by alternation or in parallel as separate formulations; or (3) by any other combination therapy regimen known in the art. When delivered in alternation therapy, the methods of the invention may comprise administering or delivering the compound or salt of Formula I and an additional active agent sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used.

Methods of treatment and pharmaceutical combinations including compounds or pharmaceutically acceptable salts of Formula I described herein together with any one or combination of the following compounds and substances as an additional active agent are provided by the disclosure:

Caspase inhibitors: IDN 6556 (Idun Pharmaceuticals)

Cyclophilin Inhibitors: for example, NIM811 (Novartis), SCY-635 (Scynexis), and DEBIO-025 (Debiopharm)

Cytochrome P450 monooxygenase inhibitors: ritonavir (WO 94/14436), ketoconazole, troleandomycin, 4-methylpyrazole, cyclosporin, clomethiazole, cimetidine, itraconazole, fluconazole, miconazole, fluvoxamine, fluoxetine, nefazodone, sertraline, indinavir, nelfinavir, amprenavir, fosamprenavir, saquinavir, lopinavir, delavirdine, erythromycin, VX-944, and VX-497. Preferred CYP inhibitors include ritonavir, ketoconazole, troleandomycin, 4-methyl pyrazole, cyclosporin, and clomethiazole Glucocorticoids: hydrocortisone, cortisone, prednisone, prednisolone, methylprednisolone, triamcinolone, paramethasone, betamethasone, and dexamethasone HCV Protease Inhibitors: for example ACH-1625 and ACH-2684, ABT-450 (Abbott), ACL-181 and AVL-192 (Avila), BI-335 (Boehringer Ingelheim), BMS-032 (Bristol Meyers Squibb), boceprevir (Merck), TMC-435, MK-7152 (Merck), GS-9256 (Gilead), GS-9451 (Gilead), R7227 (Roche), VX-950 (telaprevir, Vertex), VX-985 (Vertex), TMC-435 (Tibotec), GW-433908 (prodrug of Amprenavir, Glaxo/Vertex), indinavir (CRIXIVAN, Merck), and ITMN-191 (Intermune/Array Biopharma).

Hematopoietins: hematopoietin-1 and hematopoietin-2. Other members of the hematopoietin superfamily such as the various colony stimulating factors (e.g. (e.g. G-CSF, GM-CSF, M-CSF), Epo, and SCF (stem cell factor)

Homeopathic Therapies: Milk Thistle, silymarin, ginseng, glycyrrhizin, licorice root, schisandra, vitamin C, vitamin E, beta carotene, and selenium Immunomodulatory compounds: thalidomide, IL-2, hematopoietins, IMPDH inhibitors, for example Merimepodib (Vertex Pharmaceuticals Inc.), interferon, including natural interferon (such as OMNIFERON, Viragen and SUMIFERON, Sumitomo, a blend of natural interferons), natural interferon alpha (ALFERON, Hemispherx Biopharma, Inc.), interferon alpha nl from lymphblastoid cells (WELLFERON, Glaxo Wellcome), oral alpha interferon, Peg-interferon, Peg-interferon alfa 2a (PEGASYS, Roche), recombinant interferon alfa 2a (ROFERON, Roche), inhaled interferon alpha 2b (AERX, Aradigm), Peg-interferon alpha 2b (ALBUFERON, Human Genome Sciences/Novartis, PEGINTRON, Schering), recombinant interferon alfa 2b (INTRON A, Schering), pegylated interferon alfa 2b (PEG-INTRON, Schering, VIRAFERONPEG, Schering), interferon beta-1a (REBIF, Serono, Inc. and Pfizer), consensus interferon alpha (INFERGEN, Valeant Pharmaceutical), interferon gamma-1b (ACTIMMUNE, Intermune, Inc.), unpegylated interferon alpha, alpha interferon, and its analogs, and synthetic thymosin alpha 1 (ZADAXIN, SciClone Pharmaceuticals Inc.), and lamdba interferon (BMS)

Immunosupressants: sirolimus (RAPAMUNE, Wyeth)

Interleukins: (IL-1, IL-3, IL-4, IL-5, IL-6, IL-10, IL-11, IL-12), LIF, TGF-beta, TNF-alpha) and other low molecular weight factors (e.g. AcSDKP, pEEDCK, thymic hormones, and minicytokines)

Interferon Enhancers: EMZ702 (Transition Therapeutics)

IRES inhibitors: VGX-410C (VGX Pharma)

Monoclonal and Polyclonal antibodies: XTL-6865 (XTL), HuMax-HepC (Genmab), Hepatitis C Immune Globin (human) (CIVACIR, Nabi Biopharmaceuticals)

Nucleoside analogues: IDX-184 (Idenix), PSI-7977 and PSI-938 (Pharmasset), INX-189 (Inhibitex), R7128 (Roche), R7348 (Roche), GS-6620 (Gilead), TMC-649 (Tibotec), Lamivudine (EPIVIR, 3TC, GlaxoSmithKline), MK-0608 (Merck), zalcitabine (HIVID, Roche US Pharmaceuticals), ribavirin (including COPEGUS (Roche), REBETOL (Schering), VILONA (ICN Pharmaceuticals, and VIRAZOLE (ICN Pharmaceuticals), and viramidine (Valeant Pharmaceuticals), an amidine prodrug of ribavirin. Combinations of nucleoside analogues may also be employed.

Non-nucleoside inhibitors: PSI-6130 (Roche/Pharmasset), ABT-333 and ABT-072 (Abbott), delaviridine (RESCRIPTOR, Pfizer), PF-868554 (Pfizer), GSK-852 (GlaxoSmithKline), IDX-325 (Idenix), ANA-598 (Anadys), VX-222 and VX-759 (Vertex), MK-3281 (Merck), BI-127 (Boehringer Ingelheim), BMS-325 (Bristol Meyers), and HCV-796 (Viropharm)

NS4a inhibitors: for example ACH-1095. US patent application no. US2007/0004711 is hereby incorporated by reference in its entirety for its teachings regarding HCV inhibitors and U.S. patent application Ser. No. 12/125,554 at pages 45-90 is hereby incorporated by reference for its teachings regarding HCV inhibitors.

NS5b inhibitors: INX-181, IDX-375, MK-3281, PSI-7977, PSI-7851, PSI-938, RG-9190, VX-222 (Vertex), and BMS-791325 (Bristol Meyers Squibb).

P7 protein inhibitor: amantadine (SYMMETREL, Endo Pharmaceuticals, Inc.)

Polymerase inhibitors: NM283 (valopicitabine) (Idenix) and NM 107 (Idenix).

Protease inhibitors: BILN-2061 (Boehringer Ingelheim), GW-433908 (prodrug of Amprenavir, Glaxo/Vertex), indinavir (CRIXIVAN, Merck), ITMN-191 (Intermune/Array Biopharma), VX950 (Vertex) and combinations comprising one or more of the foregoing protease inhibitors RNA interference: SIRNA-034 RNAi (Sirna Therapeutics)

Therapeutic Vaccines: IC41 (Intercell), IMN-0101 (Imnogenetics), GI 5005 (Globeimmune), Chronvac-C (Tripep/Inovio), ED-002 (Imnogenetics), Hepavaxx C (ViRex Medical)

TNF agonists: adalimumab (HUMIRA, Abbott), entanercept (ENBREL, Amgen and Wyeth), infliximab (REMICADE, Centocor, Inc.)

Tubulin inhibitors: Colchicine

Sphingosine-1-phosphate receptor modulators: FTY720 (Novartis)

TLR agonists: ANA-975 (Anadys Pharmaceuticals), ANA-773 (Anadys Pharmaceuticals), TLR7 agonist (Anadys Pharmaceuticals), CPG10101 (Coley), and TLR9 agonists including CPG 7909 (Coley)

Cyclophilin Inhibitors: NIM811 (Novartis) and DEBIO-025 (Debiopharm)

Patients receiving hepatitis C medications are typically given interferon together with another active agent. Thus methods of treatment and pharmaceutical combinations in which a compound of the invention is provided together with an interferon, such as pegylated interferon alfa 2a, as the additional active agents are included as embodiments. Similarly methods and pharmaceutical combinations in which ribavirin is an additional active agent are provided herein.

Additionally, methods and pharmaceutical combinations in which an NS3a protease inhibitor is the additional active agent are provided herein. The NS3a protease inhibitor may be selected from the group ACH-1625, ACH-2684, ABT-450, ACL-181, AVL-192, BI-335, BMS-032, boceprevir, TMC-435, MK-7152, GS-9256, GS-9451, R7227, VX-950, VX-985, TMC-435, GW-433908, indinavir, and ITMN-191. Similarly, methods and pharmaceutical combinations in which an NS4a inhibitor is an additional active agent are provided herein. The NS4a inhibitor may be ACH-1095.

Methods of inhibiting HCV replication in vivo comprising providing a compound or pharmaceutically acceptable salt of Formula I to a patient infected with HCV, a concentration of the compound or salt of Formula I sufficient to inhibit HCV replicon replication in vitro are included herein. In this instance the concentration includes an in vivo concentration, such as a blood or plasma concentration. The concentration of compound sufficient to inhibit HCV replicon replication in vitro may be determined from an assay of replicon replication such as the assay provided in Example 6, herein.

Methods of treatment include providing certain dosage amounts of a compound or pharmaceutically acceptable salt of Formula I to a patient. Dosage levels of each active agent of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single unit dosage form will vary depending upon the patient treated and the particular mode of administration. In certain embodiments about 0.1 mg to about 2000 mg, from about 10 mg to about 1500 mg, from about 100 mg to about 1000 mg, from about 200 mg to about 800 mg, or from about 300 to about 600 mg of a compound of Formula I and optionally from about 0.1 mg to about 2000 mg, from about 10 mg to about 1500 mg, from about 100 mg to about 1000 mg, from about 200 mg to about 800 mg, or from about 300 to about 600 mg of a compound of an additional active agent, for example an NS3a protease inhibitor such as a compound of Formula II are provided daily to a patient. It is preferred that each unit dosage form contains less than 1200 mg of active agent in total. Frequency of dosage may also vary depending on the compound used and the particular disease treated. However, for treatment of most infectious disorders, a dosage regimen of 4 times daily or less is preferred and a dosage regimen of 1 or 2 times daily is particularly preferred.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease in the patient undergoing therapy.

Packaged Formulations

Methods comprising providing a compound or salt of Formula I in a container together with instructions for using the compound to treat a patient suffering from Hepatitis C infection are included herein.

Packaged pharmaceutical compositions/combinations are also included herein. Such packaged combinations include a compound of Formula I in a container together with instructions for using the combination to treat or prevent a viral infection, such as a hepatitis C infection, in a patient.

The packaged pharmaceutical composition/combination may include one or more additional active agents. In certain embodiments the additional active agent is an NS3a protease inhibitor, such as a compound of Formula II.

The packaged pharmaceutical combination may include a compound or pharmaceutically acceptable salt of Formula I and the additional active agent provided simultaneously in a single dosage form, concomitantly in separate dosage forms, or provided in separate dosage forms for administration separated by some amount of time that is within the time in which both the compound of Formula I and the additional active agent are within the bloodstream of the patient.

The packaged pharmaceutical combination may include a compound or pharmaceutically acceptable salt of Formula I provided in a container with an additional active agent provided in the same or separate container, with instructions for using the combination to treat an HCV infection in a patient.

EXAMPLES

Abbreviations

The following abbreviations are used in the reaction schemes and synthetic examples, which follow. This list in not meant to be an all-inclusive list of abbreviations used in the application as additional standard abbreviations, which are readily understood by those skilled in the art of organic synthesis, may also be used in the synthetic schemes and examples.

ACN acetonitrile

DIEA N,N-diisopropylethylamine

DME 1,2-dimethoxyethane

DMF N,N-dimethylformamide $Et_2O$ diethyl ether

FCC flash column chromatography

HATU O-(7-azabenzotriazol-1-yl)-N,N,N',N'-tetramethyluronium hexafluorophosphate PTLC preparative thin layer chromatography rt room temperature TEA triethylamine TFA trifluoroacetic acid TPP triphenylphosphine General Considerations All nonaqueous reactions were performed under an atmosphere of dry argon gas using oven-dried glassware and anhydrous solvents. The progress of reactions and the purity of target compounds were determined using one of the following two HPLC methods: (1) 3.25-min gradient elution of increasing concentrations of acetonitrile in water (10-90%) containing 0.05% formic acid with a flow rate of 1.0 mL/min and UV detection (PDA) on a Acquity UPLC BEH C18 150×2.1 mm 1.7 μm column (method 1); and (2) 4-min gradient elution of increasing concentrations of acetonitrile in water (2-98%) containing 0.1% TFA with a flow rate of 2.5 mL/min and UV detection at 254 nm on a YMC Pack Pro C18 50×4.6 mm 5 μm column (method 2).

Example 1

Synthesis of N⁴,N⁴'-Bis(4-((4-(propylsulfonyl)piperazin-1-yl)methyl)phenyl)biphenyl-4,4'-dicarboxamide

Step 1. Preparation of tert-Butyl 4-(4-(4-bromobenzamido)benzyl)piperazine-1-carboxylate (3)

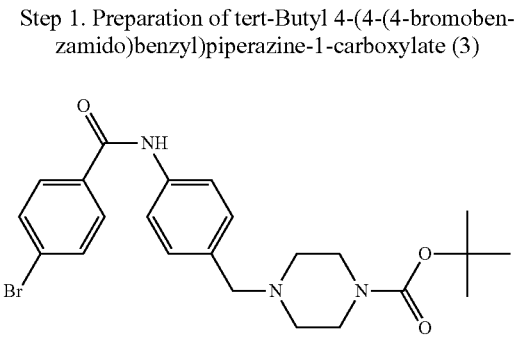

(3)

4-Bromobenzoic acid (1, 685.0 mg, 3.4 mmol) and HATU (1298.1 mg, 3.4 mmol) are partially dissolved in DMF (10 mL) at rt. DIEA (560 µL, 3.4 mmol) is added to this mixture to give a pale yellow solution. After stirring at rt for 30 min, tert-butyl 4-(4-aminobenzyl)piperazine-1-carboxylate (2, 992.9 mg, 3.4 mmol) is added and the resulting reaction mixture is heated at 60° C. for 20 h, allowed to cool to rt, and poured into water (100 mL). This mixture is extracted with Et₂O (3×150 mL). The combined organic extracts are evaporated to dryness to give a white solid, which is washed with water (50 mL) and dried in vacuo. This material is used in the next synthetic step without further purification. HPLC: tR 1.67 min (method 1). LC-MS m/z calcd for $C_{23}H_{28}{}^{79}BrN_3O_3$ ([M]+), 473. found, 474 ([M+H]+). ¹H NMR (CD₃OD): δ 1.46 (s, 9H), 2.96 (m, 4H), 3.59 (m, 4H), 4.05 (br s, 2H), 7.46 (m, 2H), 7.69 (m, 2H), 7.78 (m, 2H), 7.85 (m, 2H).

Step. 2. Preparation of 4-Bromo-N-(4-((4-(propylsulfonyl)piperazin-1-yl)methyl)phenyl)benzamide (5)

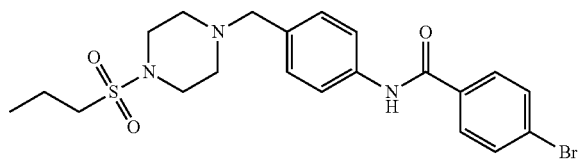

(5)

TFA (50 mL) is added in one portion at rt to a mixture of 3 (from above) partially dissolved in CH₂Cl₂ (50 mL). The resulting yellow mixture is stirred at rt for 1 h and evaporated to dryness to give the trifluoracetate salt of 4-bromo-N-(4-(piperazin-1-ylmethyl)phenyl)benzamide (4) as a brown oil. HPLC: $t_R$ 1.24 min (method 1). LC-MS m/z calcd for $C_{18}H_{20}{}^{79}BrN_3O$ ([M]+), 373. found, 374 ([M+H]+). TEA (13.5 g, excess) and 1-propanesulfonyl chloride (1.21 g, 8.5 mmol), each in single portions, are added sequentially to a mixture of 4 (from above) in CH₂Cl₂ (75 mL). The resulting solution was stirred at rt for 30 min and quenched with the addition of H₂O (75 mL). The organic layer was separated, washed with H₂O (2×75 mL), dried (Na₂SO₄), and evaporated to dryness to give crude 5 as a brown solid. This material was purified by FCC on silica (eluting with 100:10:1 v/v CHCl₃/MeOH/NH₄OH (28%); $R_f$ 0.59) to give 5 as a tan solid (1.43 g, 87% yield, 3 steps). HPLC: $t_R$ 1.80 min (method 1). LC-MS m/z calcd for $C_{21}H_{26}{}^{79}BrN_3O_3S$ ([M]+), 479. found, 480 ([M+H]+). ¹H NMR (CDCl₃): δ 1.06 (t, J=7.5 Hz, 3H), 1.86 (m, 2H), 2.51 (m, 4H), 2.87 (m, 2H), 3.28 (m, 4H), 3.52 (s, 2H), 7.31 (m, 2H), 7.58 (m, 2H), 7.62 (m, 2H), 7.74 (m, 2H), 7.82 (br s, 1H).

Step 3. Preparation of N-(4-((4-(Propylsulfonyl)piperazin-1-yl)methyl)phenyl)-4-(4,4,5,5-tetramethyl-1,3,2-dioxaborolan-2-yl)benzamide (6)

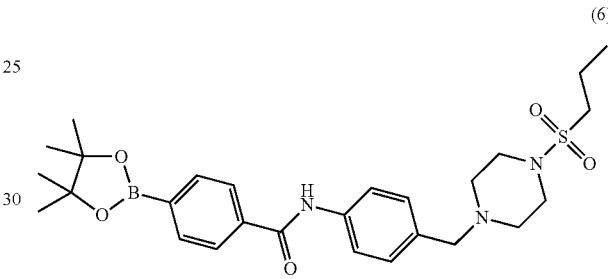

(6)

A mixture containing 5 (121.3 mg, 0.25 mmol), bis(pinacolato)diboron (138.0 mg, 0.54 mmol), Pd(TPP)₄ (12.0 mg, 0.01 mmol), and KOAc (64.7 mg, 0.66 mmol) in 1,4-dioxane (10 mL) is heated at 80° C. for 19 h, allowed to cool to rt, and evaporated to dryness. The remaining residue is reconstituted with CH₂Cl₂ (50 mL), washed with aq NaHCO₃ (1:1 v/v H₂O/sat aq NaHCO₃, 25 mL), dried, evaporated to dryness, and purified by FCC on silica (eluting with 10:1 v/v CH₂Cl₂/MeOH; $R_f$ 0.56) to give 6 as a tan solid foam (101.4 mg, 76% yield). HPLC: $t_R$ 2.33 min (method 1). LC-MS m/z calcd for $C_{27}H_{38}BN_3O_5S$ ([M]+), 527. found, 528 ([M+H]+). ¹H NMR (CDCl₃): δ 1.06 (t, J=7.5 Hz, 3H), 1.37 (s, 12H), 1.87 (m, 2H), 2.53 (m, 4H), 2.87 (m, 2H), 3.30 (m, 4H), 3.53 (s, 2H), 7.32 (m, 2H), 7.61 (m, 2H), 7.80 (br s, 1H), 7.85 (m, 2H), 7.93 (m, 2H).

Step 4. Preparation of N⁴,N⁴'-Bis(4-((4-(propylsulfonyl)piperazin-1-yl)methyl)phenyl)biphenyl-4,4'-dicarboxamide (7)

(7)

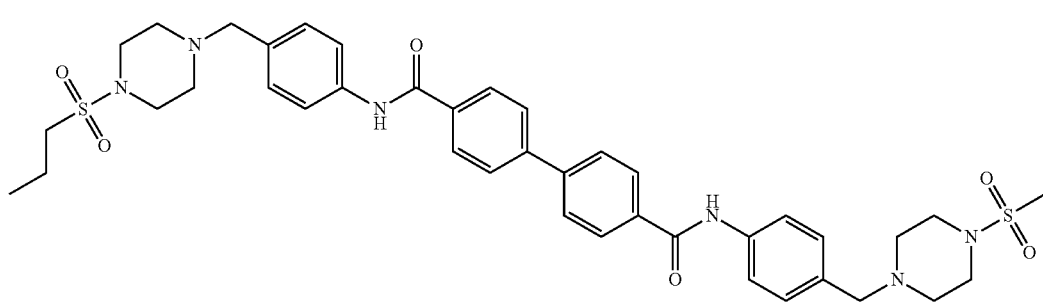

A mixture containing 5 (88.8 mg, 0.18 mmol), 6 (101.4 mg, 0.19 mmol), Pd(TPP)$_4$ (9.1 mg, 0.008 mmol), and NaHCO$_3$ (57.1 mg, 0.68 mmol) in DME/H$_2$O (4.5:1 v/v, 7 mL) was heated at 80° C. for 19 h, allowed to cool to rt, and evaporated to dryness. The remaining crude product was washed with H$_2$O (3×10 mL) and dried, then a portion (60.5 mg of the 178.1 mg isolated) was purified by PTLC to give the title product (21.9 mg). R$_f$ 0.38 (100:10:1 v/v CHCl$_3$/MeOH/NH$_4$OH (28%)). HPLC: t$_R$ 1.68 min (method 1). LC-MS m/z calcd for C$_{42}$H$_{52}$N$_6$O$_6$S$_2$ ([M]$^+$), 800. found, 801 ([M+H]$^+$). $^1$H NMR (DMSO-d$_6$): δ 0.92 (t, J=7.5 Hz, 3H), 1.62 (m, 2H), 2.38 (m, 4H), 2.95 (m, 2H), 3.10 (m, 4H), 3.44 (br s, 2H), 7.23 (m, 2H), 7.70 (m, 2H), 7.87 (m, 2H), 8.03 (m, 2H), 10.25 (s, 1H).

Example 2

(S)-Tert-Butyl 2-(4-(4'-(4-((4-(propylsulfonyl)piperazin-1-yl)methyl)phenylcarbamoyl)biphenyl-4-yl)-1H-imidazol-2-yl)pyrrolidine-1-carboxylate (8)

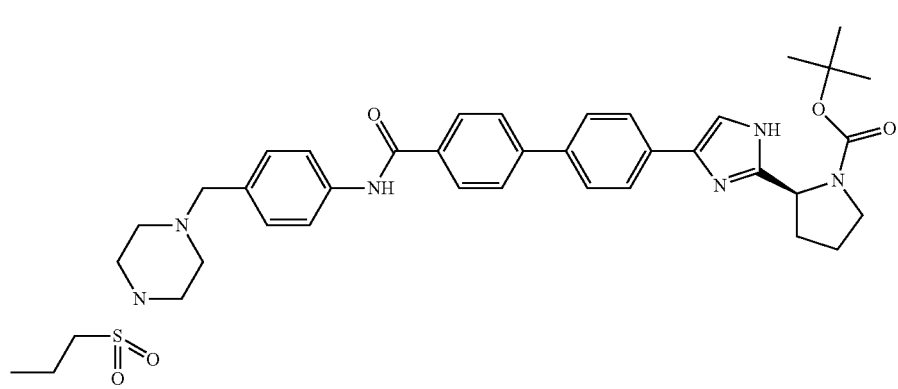

(8)

The title compound is prepared from 5 (above) and (S)-tert-butyl 2-(4-(4-(4,4,5,5-tetramethyl-1,3,2-dioxaborolan-2-yl)phenyl)-1H-imidazol-2-yl)pyrrolidine-1-carboxylate (Syngene) using the Suzuki-Miyaura cross-coupling procedure outlined above for the preparation of (7). Yield: 156.9 mg (66%). HPLC: t$_R$ 1.88 min (method 1); t$_R$ 2.28 min, 96.6% purity (method 2). LC-MS m/z calcd for C$_{39}$H$_{48}$N$_6$O$_5$S ([M]$^+$), 712. found, 713 ([M+H]$^+$). $^1$H NMR (CDCl$_3$): δ 1.06 (t, J=7.0 Hz, 3H), 1.51 (s, 9H), 1.86 (m, 2H), 1.98 (m, 1H), 2.17 (m, 2H), 2.53 (m, 4H), 2.88 (m, 2H), 3.07 (m, 1H), 3.29 (m, 4H), 3.43 (m, 2H), 3.53 (s, 2H), 4.98 (m, 1H), 7.28 (br, 1H), 7.32 (m, 2H), 7.56 (br, 1H), 7.63 (m, 2H), 7.73 (m, 2H), 7.87 (m, 2H), 7.93 (m, 2H).

Example 3

Methyl(S)-3-methyl-1-oxo-1-((5)-2-(4-(4'-(4-((4-(propylsulfonyl)piperazin-1-yl)methyl)phenylcarbamoyl)biphenyl-4-Yl)-1H-imidazol-2-yl)pyrrolidin-1-yl)butan-2-ylcarbamate (9)

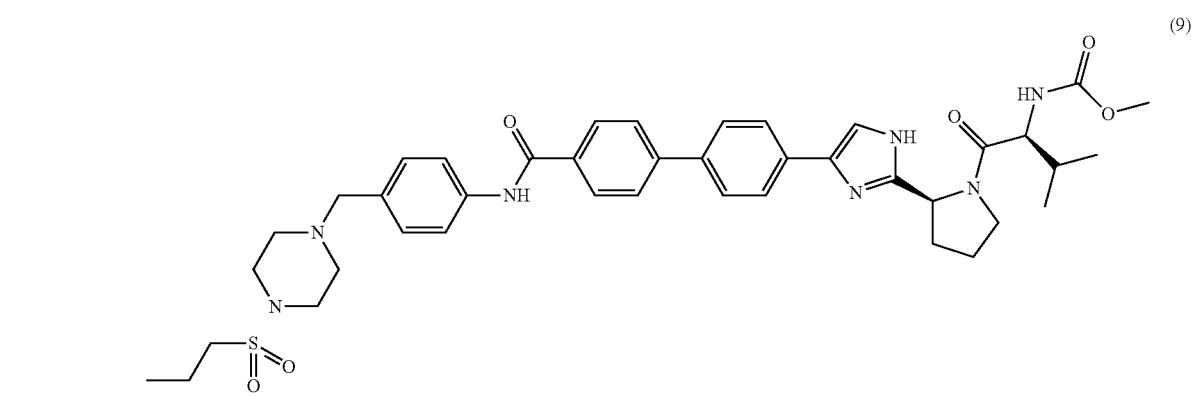

(9)

The title compound is prepared from (8) (above) and Moc-L-val-OH using the two-step TFA deprotection and HATU coupling sequence outlined above for the preparation of 5. Yield: 60.5 mg (81%, 2 steps). HPLC: t$_R$1.82 min (method 1); t$_R$ 2.17 min, 97.6% purity (method 2). LC-MS m/z calcd for C$_{41}$H$_{51}$N$_7$O$_6$S ([M]$^+$), 769. found, 770 ([M+H]$^+$). $^1$H NMR (CDCl$_3$, 50° C.): δ 0.88 (d, J=6.5 Hz, 6H), 1.06 (t, J=7.5 Hz, 3H), 1.84 (m, 2H), 1.90-2.42 (m, 4H), 2.56 (m, 4H), 2.87 (m, 2H), 3.05 (m, 1H), 3.32 (m, 4H), 3.57 (s, 2H), 3.62 (m, 1H), 3.70 (s, 3H), 3.82 (m, 1H), 4.32 (dd, J=9.0 Hz, 6.5 Hz, 1H), 5.26 (m, 1H), 5.32 (d, J=9.0 Hz, 1H), 7.24 (s, 1H), 7.32 (m, 2H), 7.61 (m, 4H), 7.67-7.87 (m, 4H), 7.93 (m, 2H).

Example 4

Synthesis of Dimethyl (2S,2'S)-1,1'-((3S,3'S)-3,3'-(4,4'-(biphenyl-4,4'-diyl)bis(1H-imidazole-4,2-diyl))bis(2-azabicyclo[2.2.1]heptane-3,2-diyl))bis(3-methyl-1-oxobutane-2,1-diyl)dicarbamate Step 1. Preparation of 1,1'-(Biphenyl-4,4'-diyl)bis(2-bromoethanone)

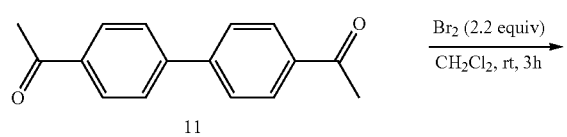

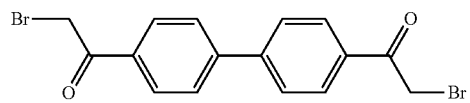

Br$_2$ (18.45 g, 115.4 mmol) is added dropwise to a stirring slurry of 11 (12.50 g, 52.5 mmol) in CH$_2$Cl$_2$ (100 mL) at rt. After 3 h, the white solid is collected by filtration, washed with CH$_2$Cl$_2$ (2×100 mL), and dried in vacuo to give the title compound (16.77 g, 74% yield). $^1$H NMR (DMSO-d$_6$): δ 4.99 (s, 4H), 7.96 (m, 4H), 8.13 (m, 4H).

Step 2. Preparation of (3S,3'S)-'3,3-2,2'-(biphenyl-4-4'-diyl)bis(2-oxoethane-2,1-diyl) 2-tert-butyl bis(2-azabicyclo[2.2.1]heptane-2,3-dicarboxylate)

(14)

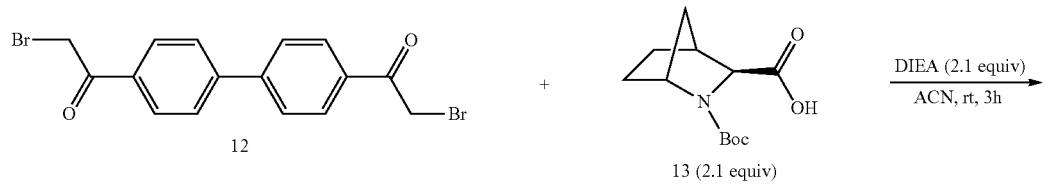

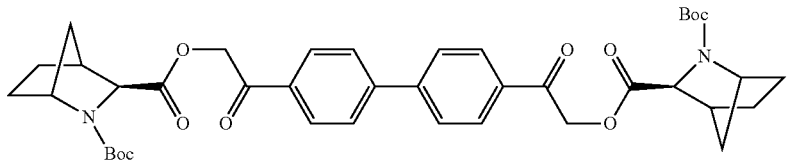

DIEA (0.80 g, 6.2 mmol) is added dropwise to a stirring mixture of 12 (1.16 g, 2.9 mmol) and (1R,3S,4S)-2-(tert-butoxycarbonyl)-2-azabicyclo[2.2.1]heptane-3-carboxylic acid (13, 6.1 mmol) in ACN at rt. After stirring for 3 h, the resulting clear solution is washed with 13 wt % aqueous NaCl (2×15 mL). The remaining organic layer, containing 14, is used directly in the next synthetic step.

Step 3. Preparation of (3S,3'S)-tert-Butyl 3,3'-(4,4'-biphenyl-4-4'-diyl)bis(1H-imidazole-4,2-diyl))bis(2-azabicyclo[2.2.1]heptane-2-carboxylate)

(15)

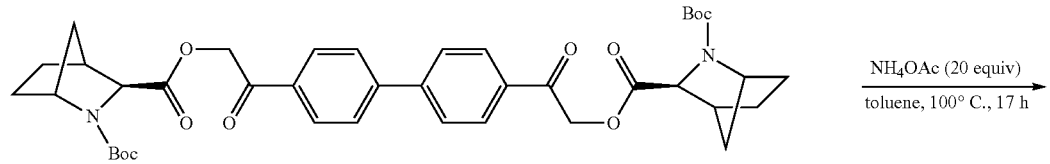

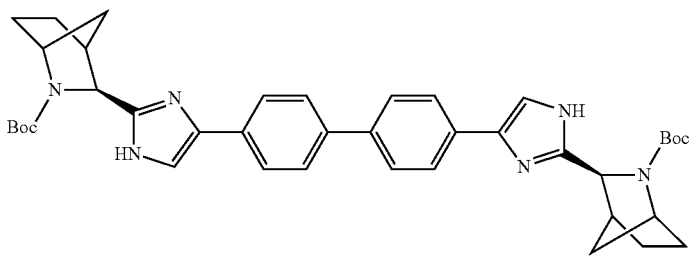

15

Toluene (25 mL) is added to a solution of 4 in ACN (from above). The resulting solution is concentrated to ~5 mL under reduced pressure; this procedure is repeated twice. The remaining solution (~5 mL) is diluted with toluene (40 mL), treated with NH$_4$OAc (4.50 g, 58.4 mmol), and heated at 100° C. for 17 h with stirring. The reaction mixture is then allowed to cool to rt and evaporated to dryness under reduced pressure. CHCl$_3$ (150 mL) and H$_2$O (100 mL) are added to the remaining residue. A saturated aq solution of NaHCO$_3$ is added dropwise to this shaken mixture until the aq layer is slightly basic (pH ~8). The separated aq layer is extracted with CHCl$_3$ (2×150 mL) and 1:1 v/v CHCl$_3$/MeOH (2×50 mL). The combined organic extracts were evaporated under reduced pressure to give crude 15 as a solid (2.2 g). This material is used without further purification in the next synthetic step. HPLC: $t_R$ 1.77 min (method 1); $t_R$ 3.64 min (method 2). LC-MS m/z calcd for C$_{40}$H$_{48}$N$_6$O$_4$ ([M]$^+$), 676. found, 677 ([M+H]$^+$).

Step 4. Preparation of (4,4'-Bis(2-((3S)-2-azabicyclo[2.2.1]heptan-3-yl)-1H-imidazol-4-yl)biphenyl (16)

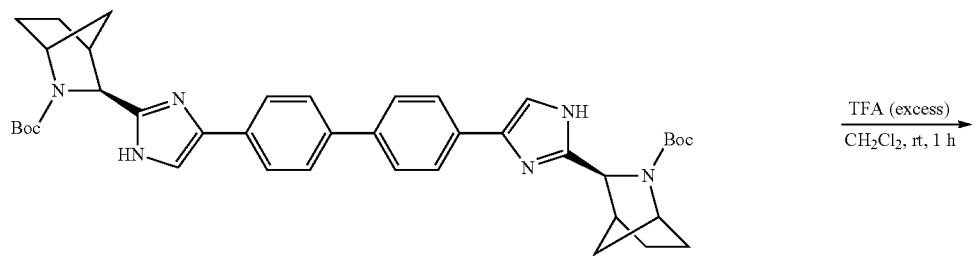

15

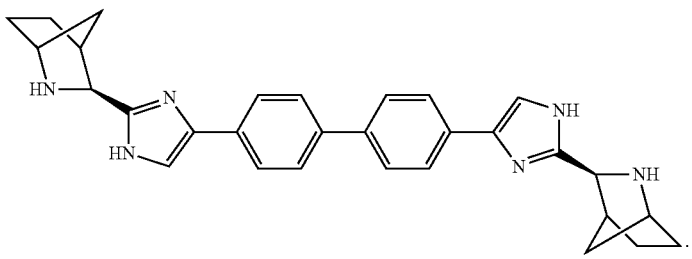

16

TFA (3 mL) is added in one portion to a stirring slurry of 15 (129.0 mg) in CH$_2$Cl$_2$ at rt. The resulting solution is stirred for 1 h and evaporated to dryness under reduced pressure to give the solid trifluoroacetate salt of 16. This material is used directly in the next synthetic step. HPLC: $t_R$ 2.83 min (method 2). LC-MS m/z calcd for C$_{30}$H$_{32}$N$_6$ ([M]$^+$), 476. found, 477 ([M+H]$^+$).

Step 5. Preparation of Dimethyl (2S,2′S)-1,1′-((3S,3′S)-3,3′-(4-4′-(biphenyl-4-4′-diyl)bis(1H-imidazole-4,2-diyl))bis(2-azabicyclo[2.2.1]heptane-3,2-diyl))bis(3-methyl-1-oxubutane-2,1-diyl)dicarbamate)

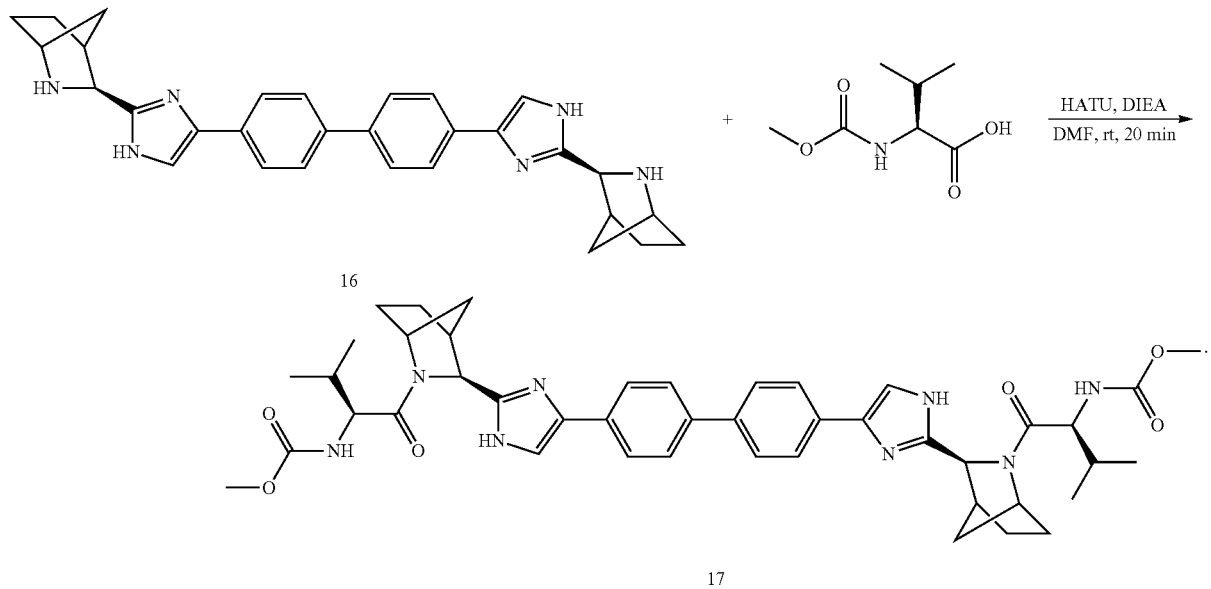

DIEA (0.50 g) is added to a mixture of (S)-2-(methoxycarbonylamino)-3-methylbutanoic acid (66.9 mg), 16 (from above), and HATU (145.6 mg) in DMF (2.5 mL) at rt. The resulting solution is stirred for 20 min and then concentrated under reduced pressure and elevated temperature (~5 mm Hg, 50° C.) to give an oil. This material is purified by FCC on silica (eluting with 100:10:1 v/v CHCl$_3$/MeOH/NH$_4$OH (28%)). A potion of this material is further purified by preparative HPLC to give the trifluoracetate salt of the final product (white solid). HPLC: t$_R$ 1.39 min (method 1); purity >99%. LC-MS m/z calcd for C$_{44}$H$_{54}$N$_8$O$_6$ ([M]$^+$), 790. found, 791 ([M+H]$^+$).

Example 5

Additional NS5a Inhibitors

The additional NS5a Inhibitors, shown in TABLE I, are prepared by the methods set forth in Examples 1 to 4.

| Cmp. | Structure | Name | EC50 (uM) |
|---|---|---|---|
| 17 | 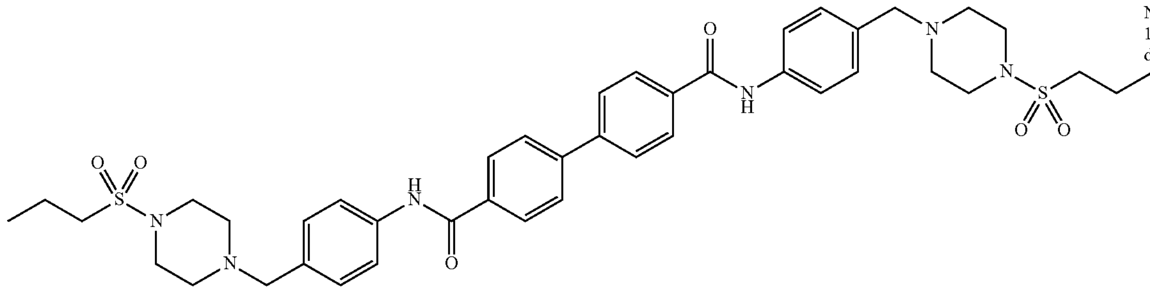 [SMILES: CCCS(=O)(=O)N1CCN(Cc2ccc(NC(=O)c3ccc(-c4ccc(C(=O)Nc5ccc(CN6CCN(S(=O)(=O)CCC)CC6)cc5)cc4)cc3)cc2)CC1] | N4,N4'-bis(4-((4-(propylsulfonyl)piperazin-1-yl)methyl)phenyl)biphenyl-4,4'-dicarboxamide | ** |
| 18 | 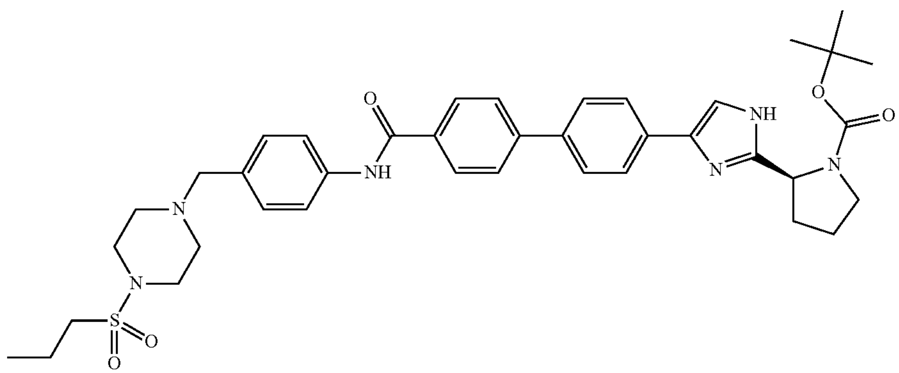 [SMILES: CCCS(=O)(=O)N1CCN(Cc2ccc(NC(=O)c3ccc(-c4ccc(-c5c[nH]c([C@@H]6CCCN6C(=O)OC(C)(C)C)n5)cc4)cc3)cc2)CC1] | (S)-tert-butyl 2-(4-(4'-(4-((4-(propylsulfonyl)piperazin-1-yl)methyl)phenylcarbamoyl)biphenyl-4-yl)-1H-imidazol-2-yl)pyrrolidine-1-carboxylate | ** |

| Cmp. | Structure | Name | EC50 (uM) |
|---|---|---|---|
| 19 | 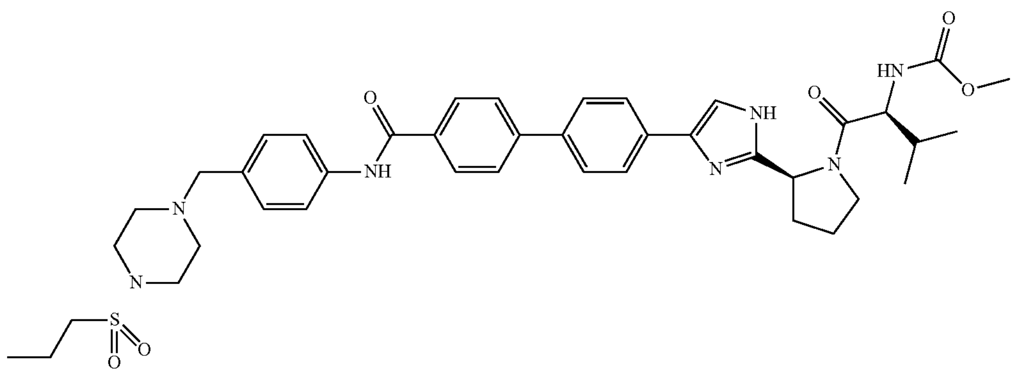 | methyl (S)-3-methyl-1-oxo-1-((S)-2-(4-(4'-(4-((4-(propylsulfonyl)piperazin-1-yl)methyl)phenylcarbamoyl)biphenyl-4-yl)-1H-imidazol-2-yl)pyrrolidin-1-yl)butan-2-ylcarbamate | ** |
| 20 | 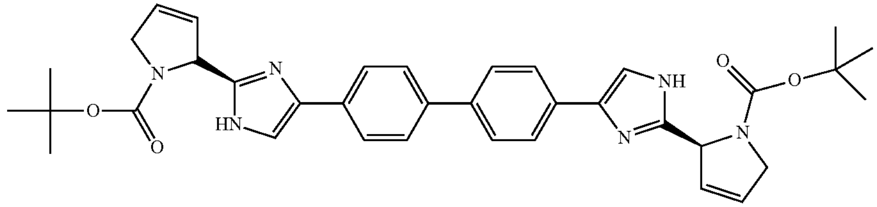 | (2R,2'R)-tert-butyl 2,2'-(4,4'-(biphenyl-4,4'-diyl)bis(1H-imidazole-4,2-diyl))bis(2,5-dihydro-1H-pyrrole-1-carboxylate) | * |
| 21 | 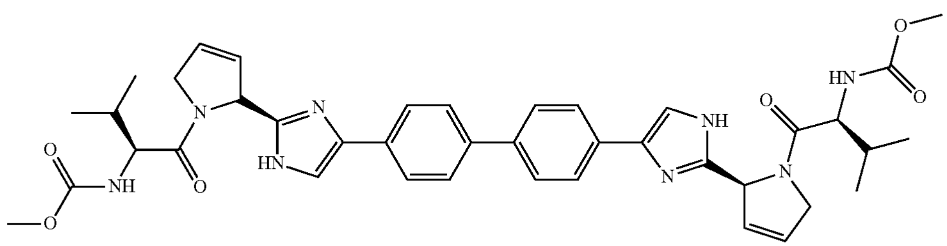 | dimethyl (2S,2'S)-1,1'-((2R,2'R)-2,2'-(4,4'-(biphenyl-4,4'-diyl)bis(1H-imidazole-4,2-diyl))bis(1H-pyrrole-2,1(2H,5H)-diyl))bis(3-methyl-1-oxobutane-2,1-diyl)dicarbamate | *** |

-continued

| Cmp. | Structure | Name | EC50 (uM) |
|---|---|---|---|
| 22 | 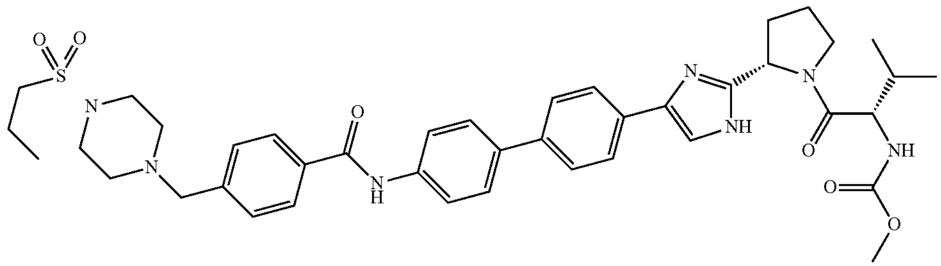 | methyl (S)-3-methyl-1-oxo-1-((S)-2-(4-(4'-(4-((4-(propylsulfonyl)piperazin-1-yl)methyl)benzamido)biphenyl-4-yl)-1H-imidazol-2-yl)pyrrolidin-1-yl)butan-2-ylcarbamate | *** |
| 23 | 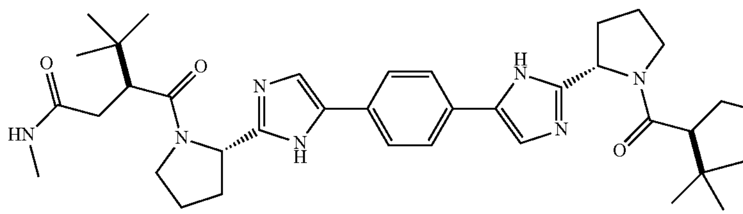 | (3S,3'S)-3,3'-(2S,2'S)-2,2'-(5,5'-(1,4-phenylene)bis(1H-imidazole-5,2-diyl))bis(pyrrolidine-2,1-diyl))bis(oxomethylene)bis(N,4,4-trimethylpentanamide) | ** |
| 24 | 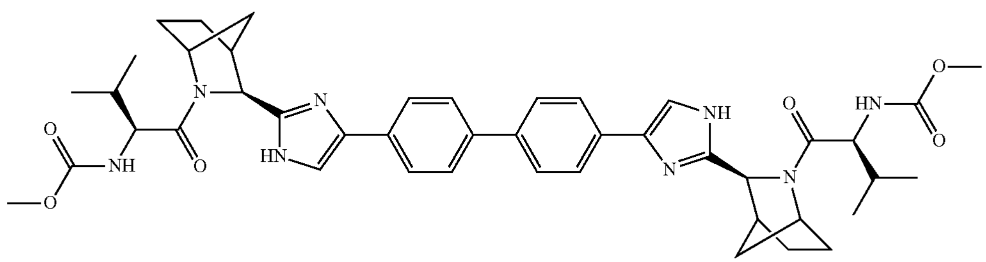 | dimethyl (2S,2'S)-1,1'-((3S,3'S)-3,3'-(4,4'-(biphenyl-4,4'-diyl)bis(1H-imidazole-4,2-diyl))bis(2-azabicyclo[2.2.1]heptane-3,2-diyl))bis(3-methyl-1-oxobutane-2,1-diyl)dicarbamate | *** |
| 25 | 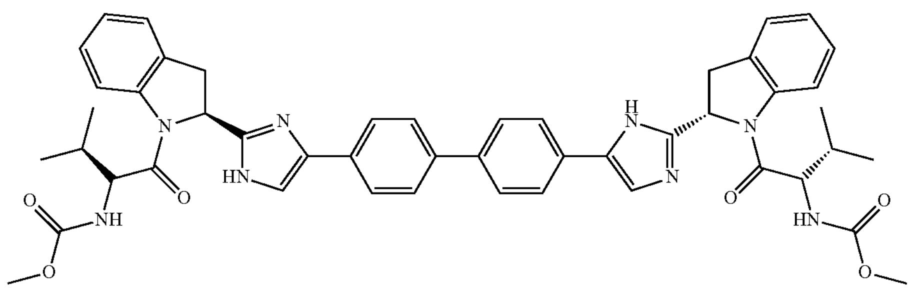 | dimethyl (2R,2'R)-1,1'-((2S,2'S)-2,2'-(5,5'-(biphenyl-4,4'-diyl)bis(1H-imidazole-5,2-diyl))bis(indoline-2,1-diyl))bis(3-methyl-1-oxobutane-2,1-diyl)dicarbamate | *** |

-continued

| Cmp. | Structure | Name | EC50 (uM) |
|---|---|---|---|
| 26 | 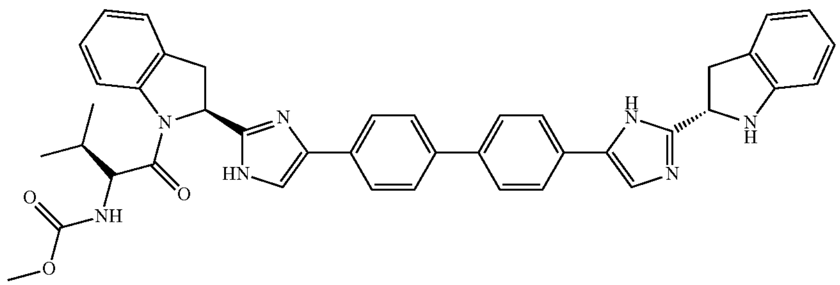 | methyl (R)-1-((S)-2-(4-(4'-(2-(2-((S)-indolin-2-yl)-1H-imidazol-5-yl)biphenyl-4-yl)-1H-imidazol-2-yl)indolin-1-yl)-3-methyl-1-oxobutan-2-yl)carbamate | *** |
| 27 | 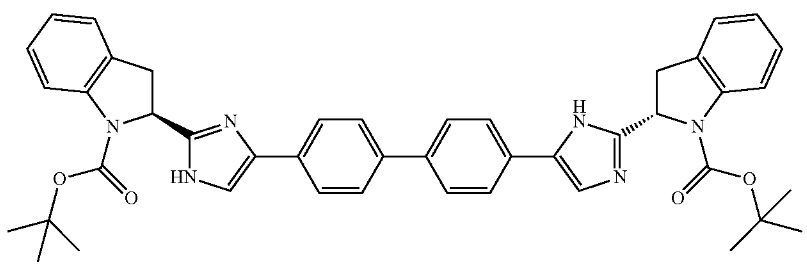 [SMILES: CC(C)(C)OC(=O)N1c2ccccc2C[C@H]1c1nc(-c2ccc(-c3ccc(-c4cnc([C@@H]5Cc6ccccc6N5C(=O)OC(C)(C)C)[nH]4)cc3)cc2)c[nH]1] | (2S,2'S)-tert-butyl 2,2'-(5,5'-(biphenyl-4,4'-diyl)bis(1H-imidazole-5,2-diyl))diindoline-1-carboxylate | ** |
| 28 | 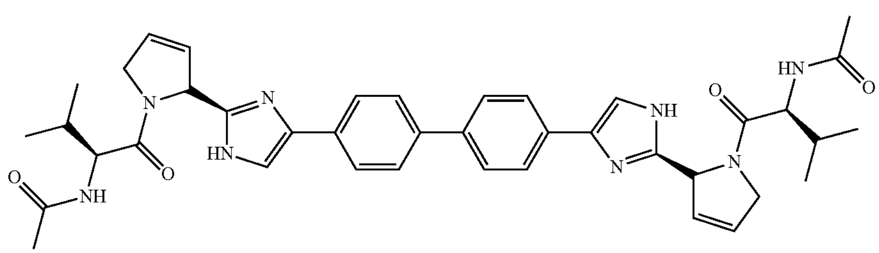 | N,N'-(2S,2'S)-1,1'-((2R,2'R)-2,2'-(4,4'-(biphenyl-4,4'-diyl)bis(1H-imidazole-4,2-diyl))bis(1H-pyrrole-2,1(2H,5H)-diyl))bis(3-methyl-1-oxobutane-2,1-diyl)diacetamide | ** |

-continued

| Cmp. | Structure | Name | EC50 (uM) |
|---|---|---|---|
| 29 | 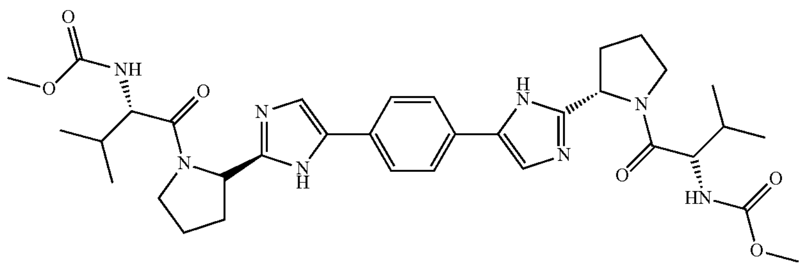 | dimethyl (2S,2'S)-1,1'-((2S,2'S)-2,2'-(5,5'-(1,4-phenylene)bis(1H-imidazole-5,2-diyl))bis(pyrrolidine-2,1-diyl))bis(3-methyl-1-oxobutane-2,1-diyl)dicarbamate | NA |
| 30 | 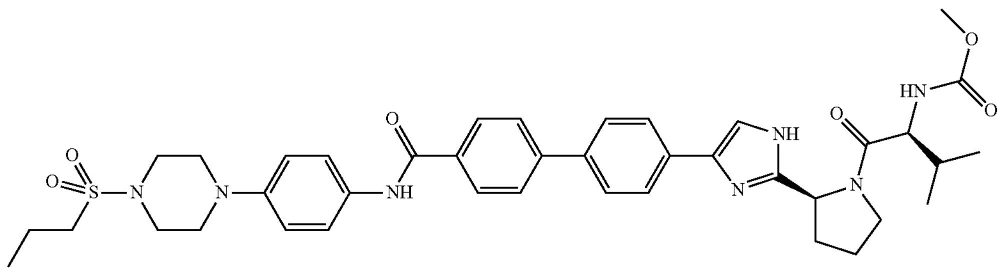 [SMILES: CCCS(=O)(=O)N1CCN(c2ccc(NC(=O)c3ccc(-c4ccc(-c5c[nH]c([C@@H]6CCCN6C(=O)[C@@H](NC(=O)OC)C(C)C)n5)cc4)cc3)cc2)CC1] | methyl (S)-3-methyl-1-oxo-1-((S)-2-(4-(4'-(4-(propylsulfonyl)piperazin-1-yl)phenylcarbamoyl)biphenyl-4-yl)-1H-imidazol-2-yl)pyrrolidin-1-yl)butan-2-ylcarbamate | NA |
| 31 | 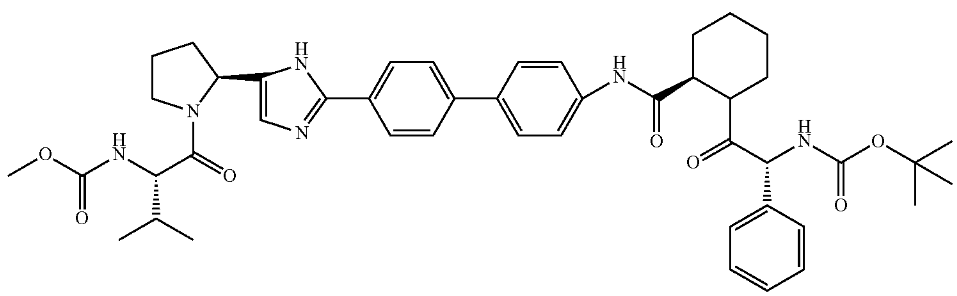 [SMILES: COC(=O)N[C@H](C(=O)N1CCC[C@H]1c1cnc(-c2ccc(-c3ccc(NC(=O)[C@H]4CCCCC4C(=O)[C@H](NC(=O)OC(C)(C)C)c4ccccc4)cc3)cc2)[nH]1)C(C)C] | | NA |

-continued

| Cmp. | Structure | Name | EC50 (uM) |
|---|---|---|---|
| 32 | 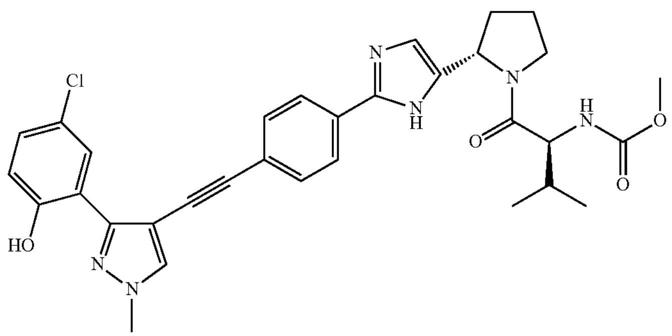 | methyl (S)-1-((S)-2-(2-(4-((3-(5-chloro-2-hydroxyphenyl)-1-methyl-1H-pyrazol-4-yl)ethynyl)phenyl)-1H-imidazol-5-yl)pyrrolidin-1-yl)-3-methyl-1-oxobutan-2-yl)carbamate | NA |
| 33 | 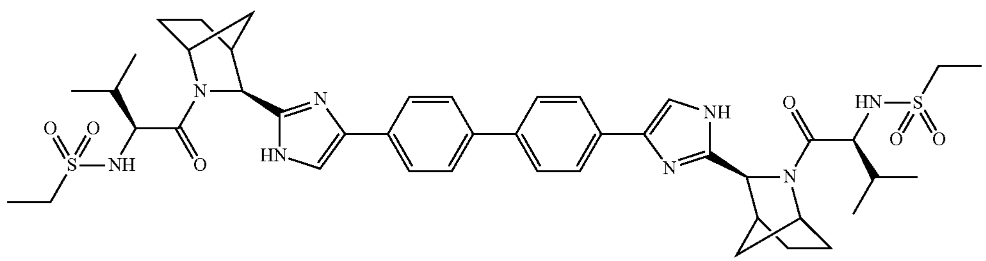 [SMILES: CCS(=O)(=O)N[C@H](C(=O)N1C2CCC(C2)[C@H]1c1nc(-c2ccc(-c3ccc(-c4c[nH]c([C@@H]5C6CCC(C6)N5C(=O)[C@@H](NS(=O)(=O)CC)C(C)C)n4)cc3)cc2)c[nH]1)C(C)C] | N,N'-(2S,2'S)-1,1'-((3S,3'S)-3,3'-(4,4'-(biphenyl-4,4'-diyl)bis(1H-imidazole-4,2-diyl))bis(2-azabicyclo[2.2.1]heptane-3,2-diyl))bis(3-methyl-1-oxobutane-2,1-diyl)diethanesulfonamide | *** |
| 34 | 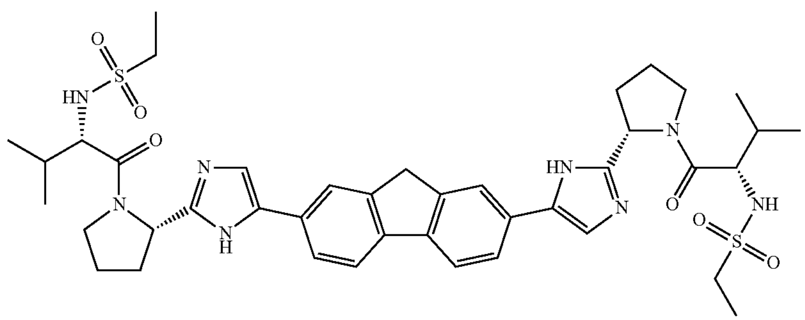 [SMILES: CCS(=O)(=O)N[C@H](C(=O)N1CCC[C@H]1c1ncc(-c2ccc3c(c2)Cc2cc(-c4cnc([C@@H]5CCCN5C(=O)[C@@H](NS(=O)(=O)CC)C(C)C)[nH]4)ccc2-3)[nH]1)C(C)C] | N,N'-(2S,2'S)-1,1'-((2S,2'S)-2,2'-(5,5'-(9H-fluorene-2,7-diyl)bis(1H-imidazole-5,2-diyl))bis(pyrrolidine-2,1-diyl))bis(3-methyl-1-oxobutane-2,1-diyl)diethanesulfonamide | |

-continued

| Cmp. | Structure | Name | EC50 (uM) |
|---|---|---|---|
| 35 | 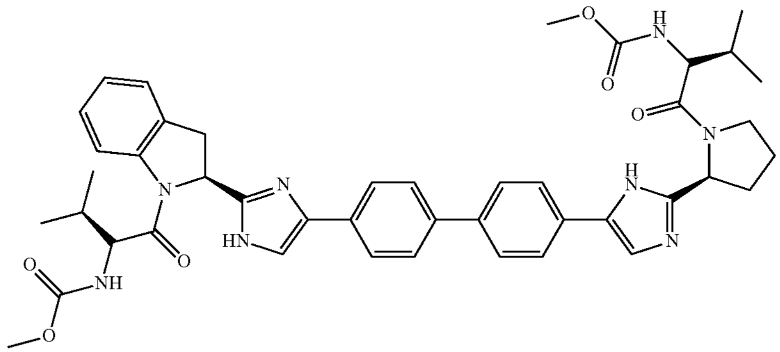 | | *** |
| 36 | 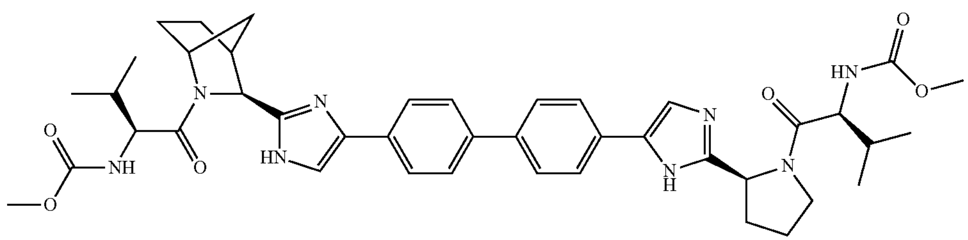 | | ** |
| 37 | 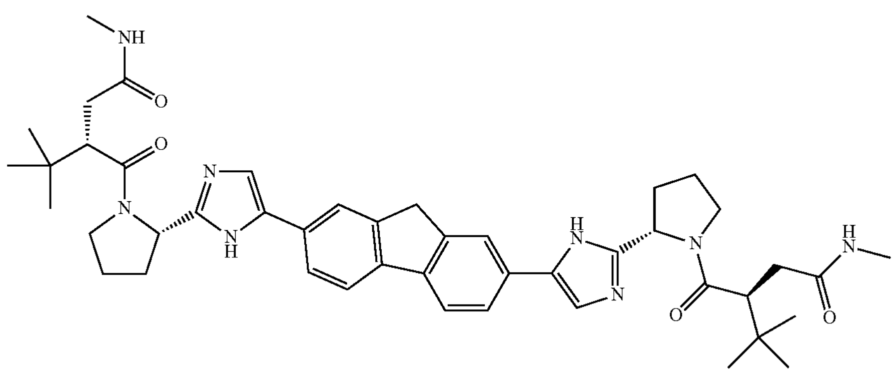 [SMILES: CNC(=O)C[C@H](C(=O)N1CCC[C@H]1c1ncc(-c2ccc3c(c2)Cc2cc(-c4cnc([C@@H]5CCCN5C(=O)[C@@H](CC(=O)NC)C(C)(C)C)[nH]4)ccc2-3)[nH]1)C(C)(C)C] | (3S,3′S)-3,3′-(2S,2′S)-2,2′-(5,5′-(9H-fluorene-2,7-diyl)bis(1H-imidazole-5,2-diyl))bis(pyrrolidine-2,1-diyl)bis(oxomethylene)bis(N,4,4-trimethyl)pentanamide) | >0.001 |

-continued

| Cmp. | Structure | Name | EC50 (uM) |
|---|---|---|---|
| 38 | 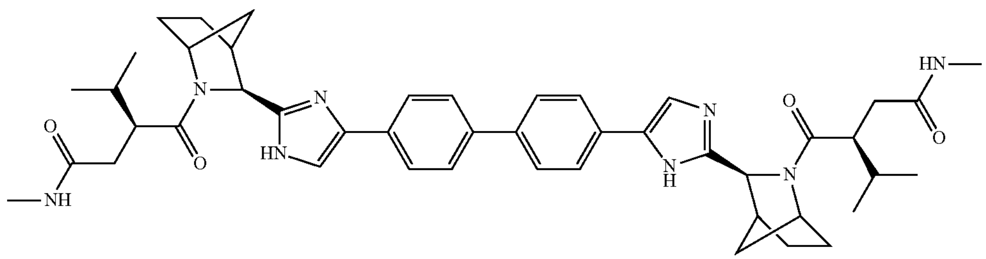 | (3S,3'S)-3,3'-(3S,3'S)-3,3'-(4,4'-(biphenyl-4,4'-diyl)bis(1H-imidazole-4,2-diyl))bis(2-azabicyclo[2.2.1]heptane-3,2-diyl)bis(oxomethylene)bis(N,4-dimethylpentanamide) | >0.001 |
| 39 | 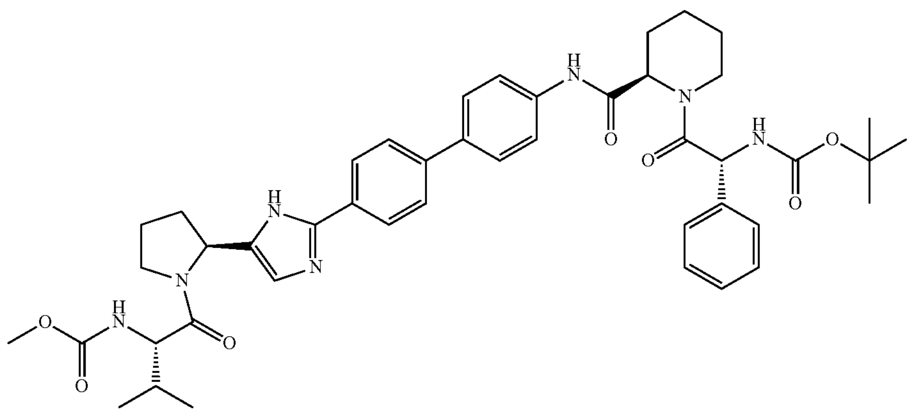 [SMILES: COC(=O)N[C@H](C(=O)N1CCC[C@H]1c1cnc(-c2ccc(-c3ccc(NC(=O)[C@H]4CCCCN4C(=O)[C@H](NC(=O)OC(C)(C)C)c4ccccc4)cc3)cc2)[nH]1)C(C)C] | | >0.001 |
| 40 | 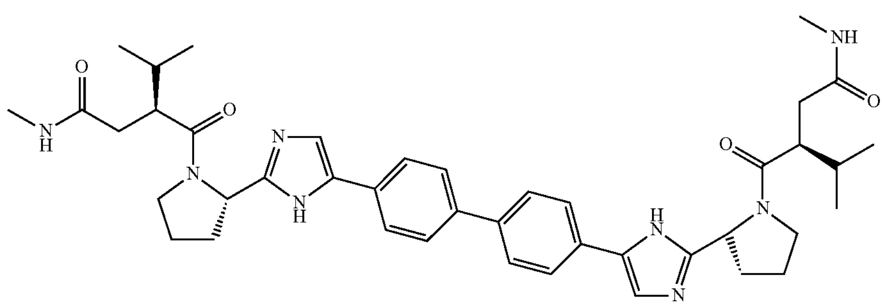 | (S)-3-((R)-2-(5-(4'-(2-((S)-1-((S)-2-isopropyl-4-(methylamino)-4-oxobutanoyl)pyrrolidin-2-yl)-1H-imidazol-5-yl)biphenyl-4-yl)-1H-imidazol-2-yl)pyrrolidine-1-carbonyl)-N,4-dimethylpentanamide | *** |

| Cmp. | Structure | Name | EC50 (uM) |
|---|---|---|---|
| 41 | 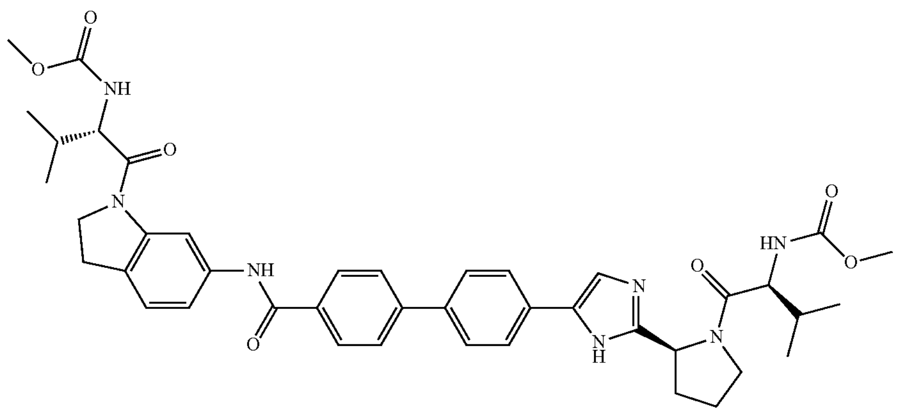 | | *** |
| 42 | 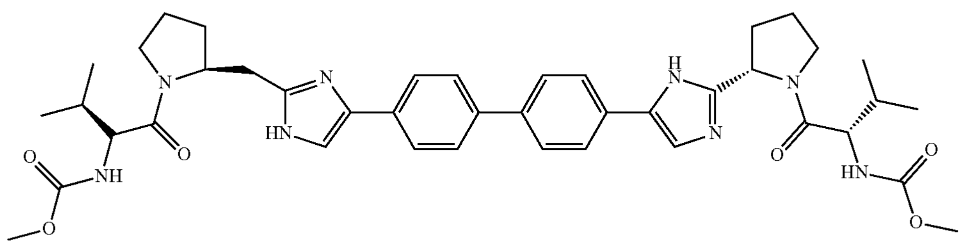 | | |
| 43 | 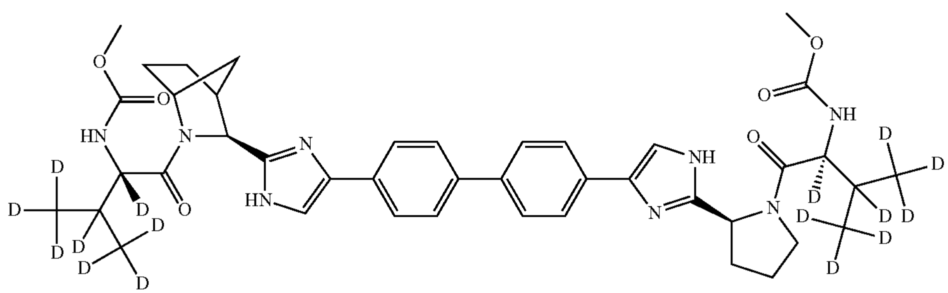 [SMILES: [2H]C([2H])([2H])C([2H])(C([2H])([2H])[2H])[C@]([2H])(NC(=O)OC)C(=O)N1CCC[C@H]1c1nc(-c2ccc(-c3ccc(-c4c[nH]c([C@@H]5C6CCC(C6)N5C(=O)[C@@]([2H])(NC(=O)OC)C([2H])(C([2H])([2H])[2H])C([2H])([2H])[2H])n4)cc3)cc2)c[nH]1] | | *** |

-continued

| Cmp. | Structure | Name | EC50 (uM) |
|---|---|---|---|
| 44 | 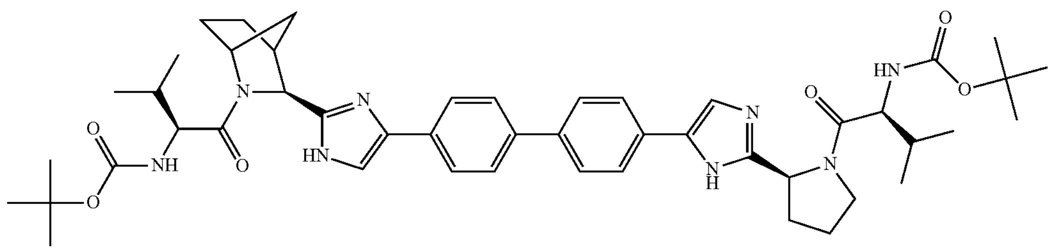 [SMILES: CC(C)[C@H](NC(=O)OC(C)(C)C)C(=O)N1CCC[C@H]1c1ncc(-c2ccc(-c3ccc(-c4c[nH]c([C@@H]5C6CCC(C6)N5C(=O)[C@@H](NC(=O)OC(C)(C)C)C(C)C)n4)cc3)cc2)[nH]1] | | |
| 45 | 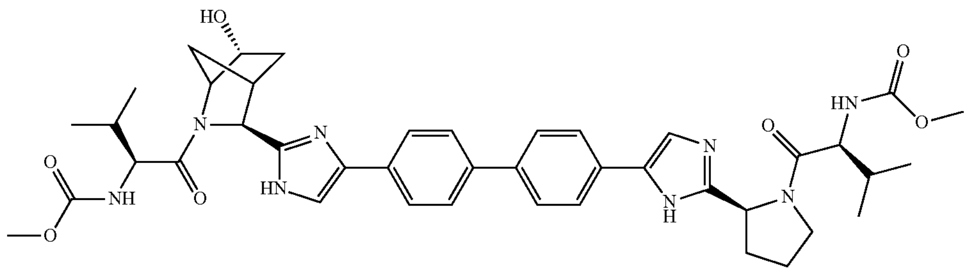 | | ** |
| 46 | 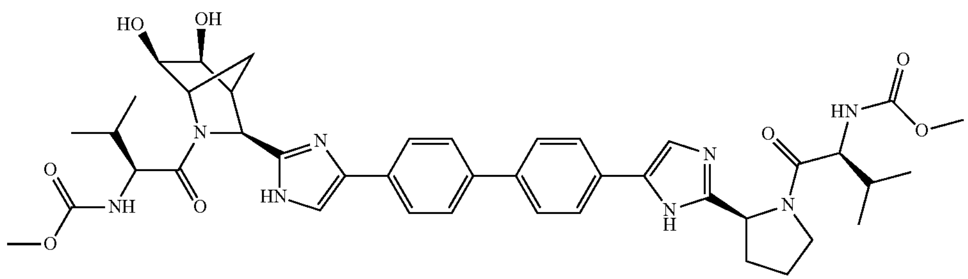 | | ** |

| Cmp. | Structure | Name | EC50 (uM) |
|---|---|---|---|
| 47 | 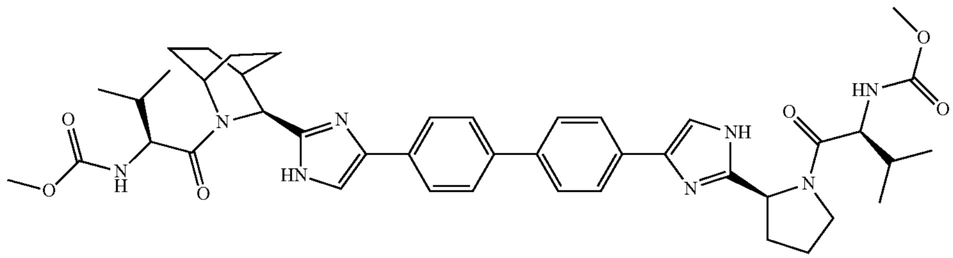 [SMILES: COC(=O)N[C@H](C(=O)N1CCC[C@H]1c1nc(-c2ccc(-c3ccc(-c4c[nH]c([C@@H]5C6CCC(CC6)N5C(=O)[C@@H](NC(=O)OC)C(C)C)n4)cc3)cc2)c[nH]1)C(C)C] | | *** |
| 48 | 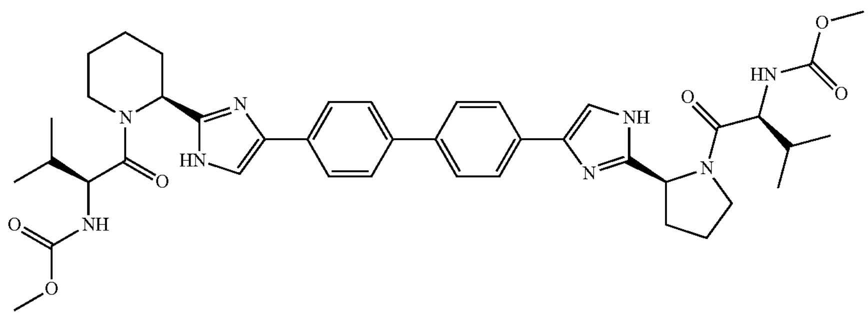 [SMILES: COC(=O)N[C@H](C(=O)N1CCCC[C@H]1c1nc(-c2ccc(-c3ccc(-c4c[nH]c([C@@H]5CCCN5C(=O)[C@@H](NC(=O)OC)C(C)C)n4)cc3)cc2)c[nH]1)C(C)C] | | *** |
| 49 | 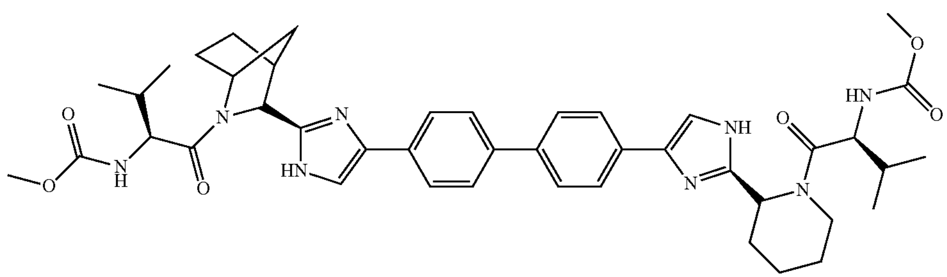 | | *** |

-continued

| Cmp. | Structure | Name | EC50 (uM) |
|---|---|---|---|
| 50 | 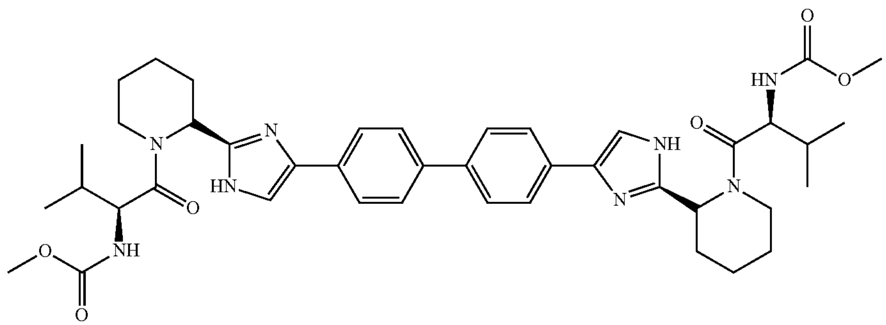 | | *** |
| 51 | 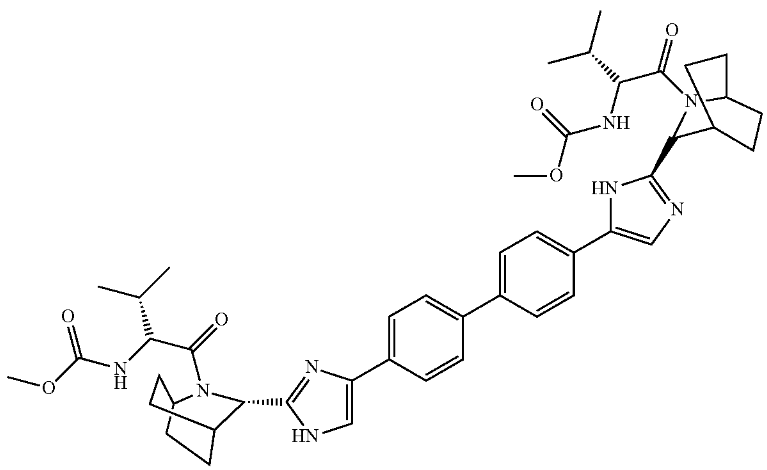 | | *** |

| Cmp. | Structure | Name | EC50 (uM) |
|---|---|---|---|
| 52 | 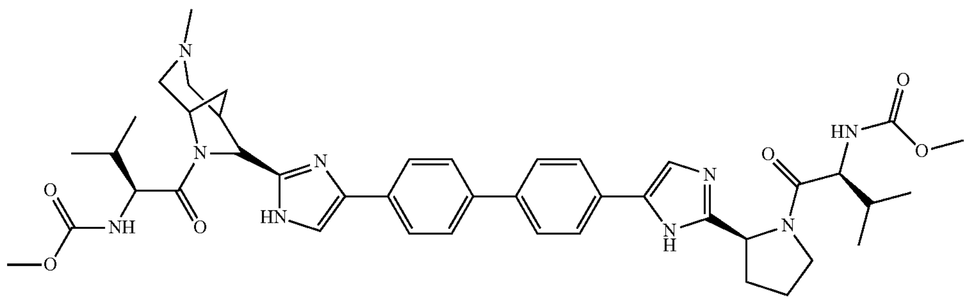 | | ** |
| 53 | 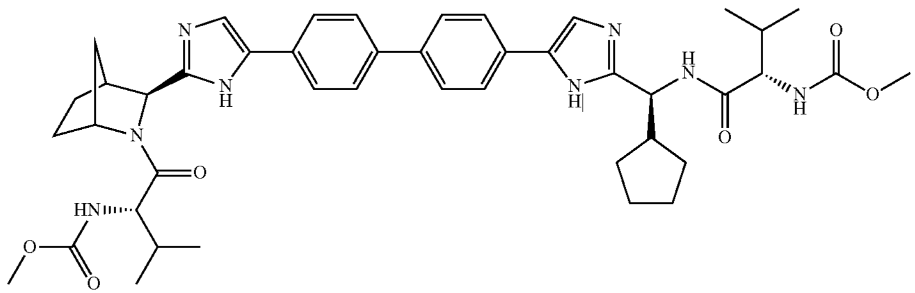 | | *** |
| 54 | 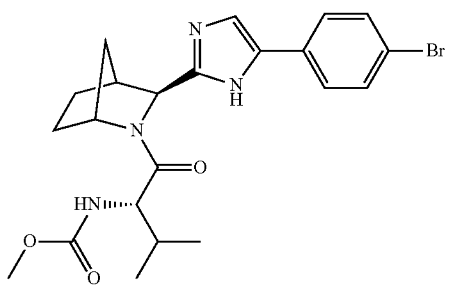 [SMILES: COC(=O)N[C@H](C(=O)N1C2CCC(C2)[C@H]1c1ncc(-c2ccc(Br)cc2)[nH]1)C(C)C] | methyl (2S)-1-((3S)-3-(5-(4-bromophenyl)-1H-imidazol-2-yl)-2-azabicyclo[2.2.1]heptan-2-yl)-3-methyl-1-oxobutan-2-ylcarbamate | <0.1 |

-continued

| Cmp. | Structure | Name | EC50 (uM) |
|---|---|---|---|
| 55 | 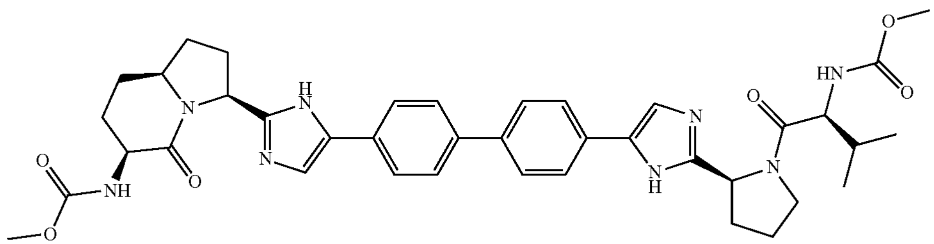 | | ** |
| 56 | 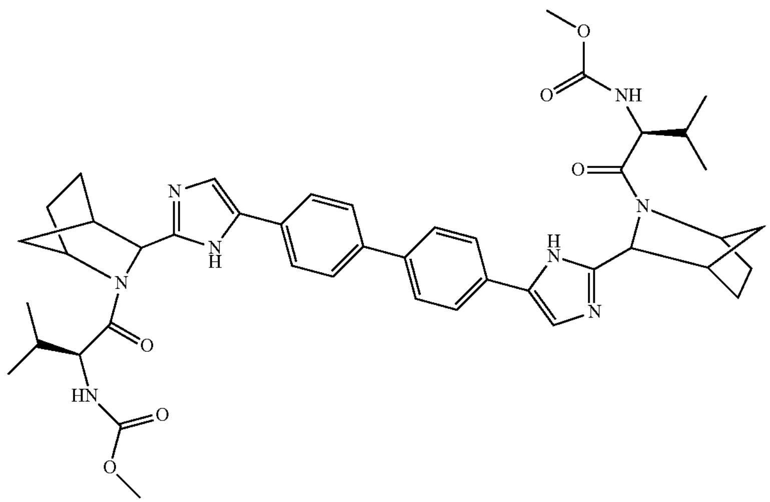 [SMILES: COC(=O)N[C@H](C(=O)N1C2CCC(C2)C1c1ncc(-c2ccc(-c3ccc(-c4cnc(C5C6CCC(C6)N5C(=O)[C@@H](NC(=O)OC)C(C)C)[nH]4)cc3)cc2)[nH]1)C(C)C] | dimethyl (2S,2'S)-1,1'-(3,3'-(5,5'-(biphenyl-4,4'-diyl)bis(1H-imidazole-5,2-diyl))bis(2-azabicyclo[2.2.1]heptane-3,2-diyl))bis(3-methyl-1-oxobutane-2,1-diyl)dicarbamate | *** |

-continued

| Cmp. | Structure | Name | EC50 (uM) |
|---|---|---|---|
| 57 | 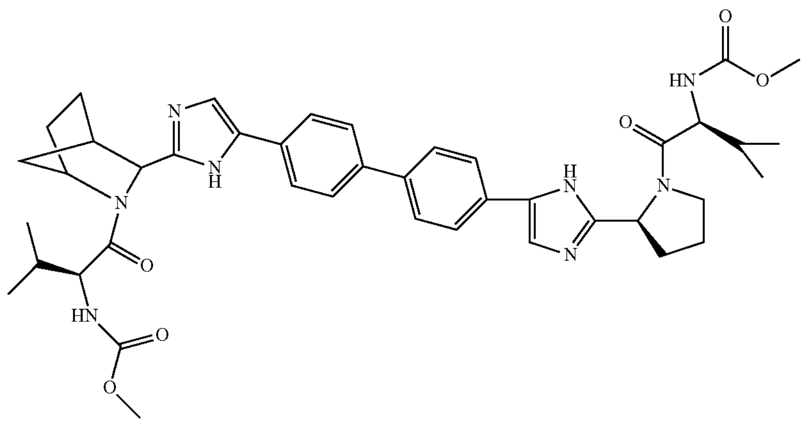 [SMILES: COC(=O)N[C@H](C(=O)N1C2CCC(C2)C1c1ncc(-c2ccc(-c3ccc(-c4cnc([C@@H]5CCCN5C(=O)[C@@H](NC(=O)OC)C(C)C)[nH]4)cc3)cc2)[nH]1)C(C)C] | | *** |
| 58 | 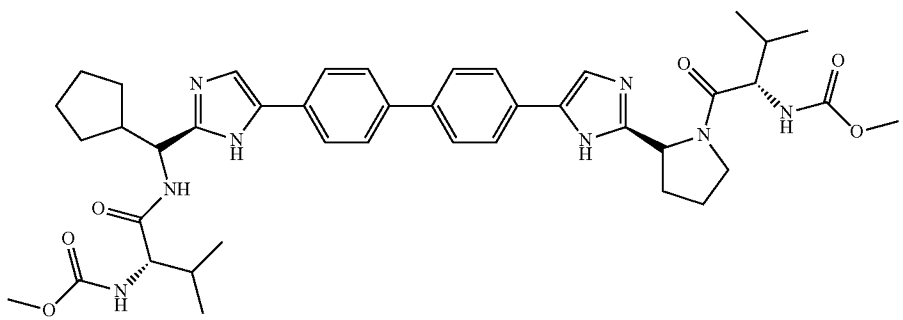 | | |
| 59 | 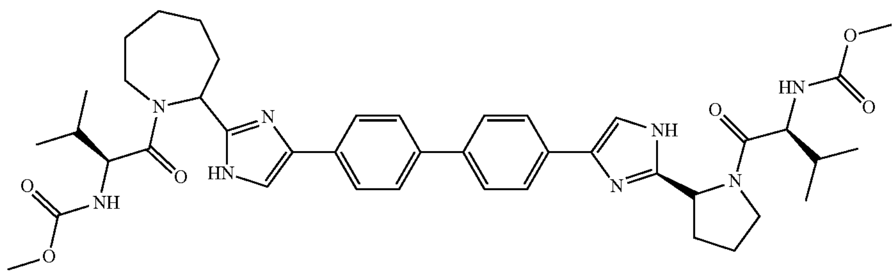 | | *** |

| Cmp. | Structure | Name | EC50 (uM) |
|---|---|---|---|
| 60 | 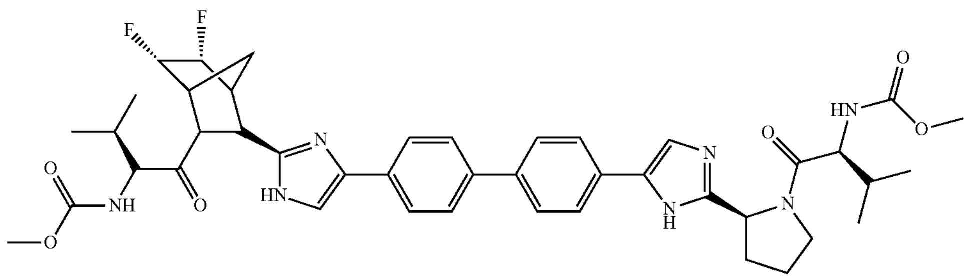 | | *** |
| 61 | 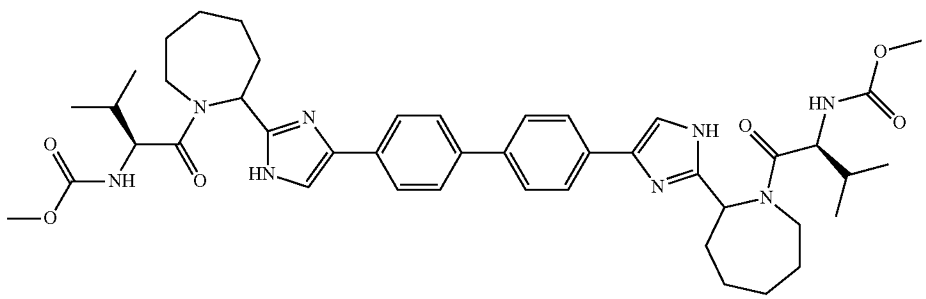 | dimethyl (2S,2'S)-1,1'-(2,2'-(4,4'-(biphenyl-4,4'-diyl)bis(1H-imidazole-4,2-diyl))bis(azepane-2,1-diyl))bis(3-methyl-1-oxobutane-2,1-diyl)dicarbamate | ** |
| 62 | 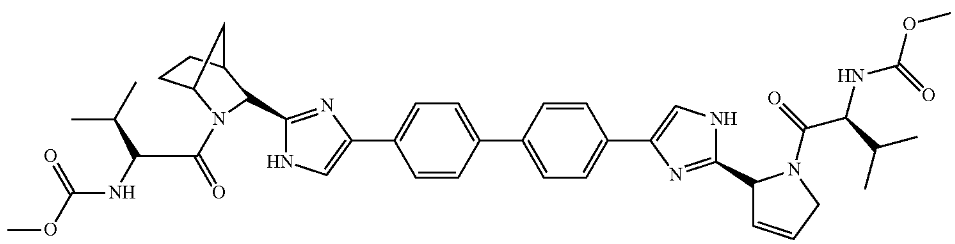 | | *** |

-continued

| Cmp. | Structure | Name | EC50 (uM) |
|---|---|---|---|
| 63 | 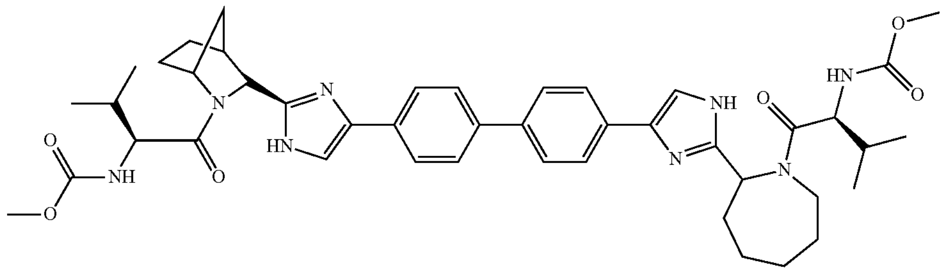 | | *** |
| 64 | 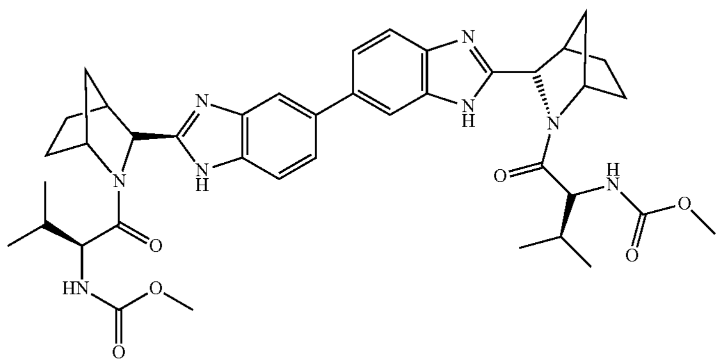 | | 0.619 |
| 65 | 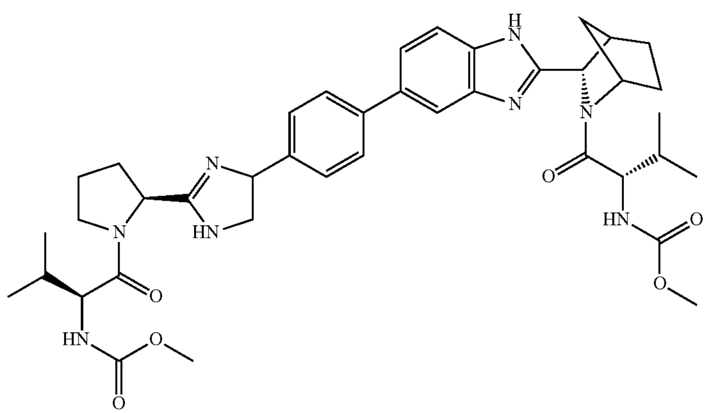 [SMILES: COC(=O)N[C@H](C(=O)N1CCC[C@H]1C1=NC(c2ccc(-c3ccc4[nH]c([C@@H]5C6CCC(C6)N5C(=O)[C@@H](NC(=O)OC)C(C)C)nc4c3)cc2)CN1)C(C)C] | | *** |

-continued

| Cmp. | Structure | Name | EC50 (uM) |
|---|---|---|---|
| 66 | 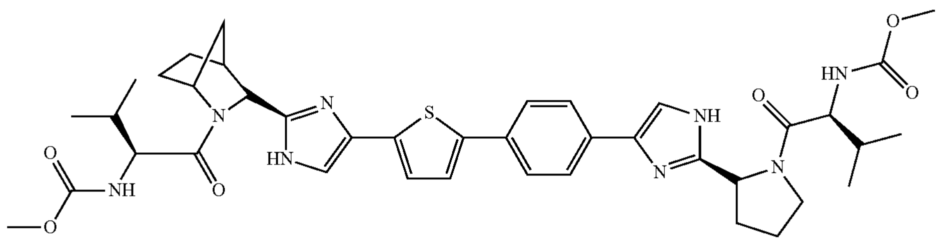 | | |
| 67 | 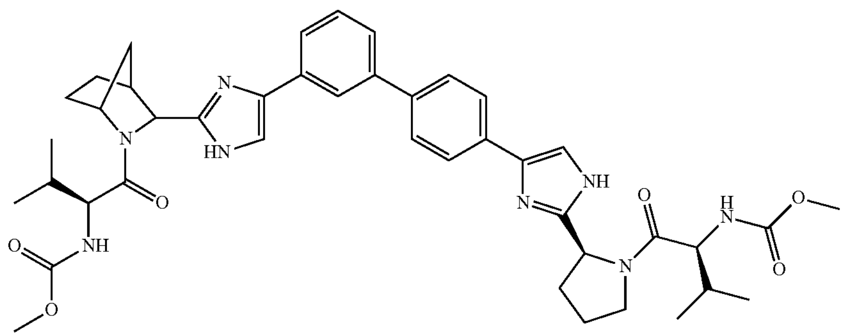 [SMILES: COC(=O)N[C@H](C(=O)N1C2CCC(C2)C1c1nc(-c2cccc(-c3ccc(-c4c[nH]c([C@@H]5CCCN5C(=O)[C@@H](NC(=O)OC)C(C)C)n4)cc3)c2)c[nH]1)C(C)C] | | |
| 68 | 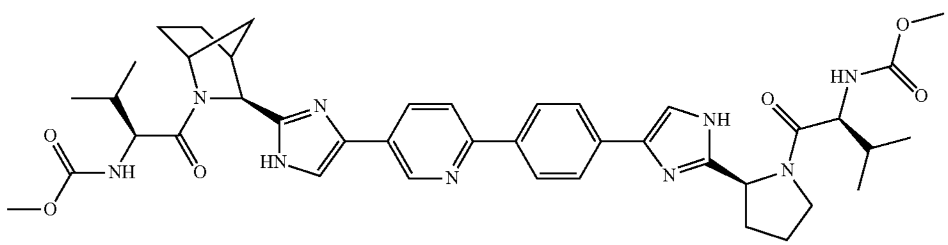 | | |

-continued

| Cmp. | Structure | Name | EC50 (uM) |
|---|---|---|---|
| 69 | 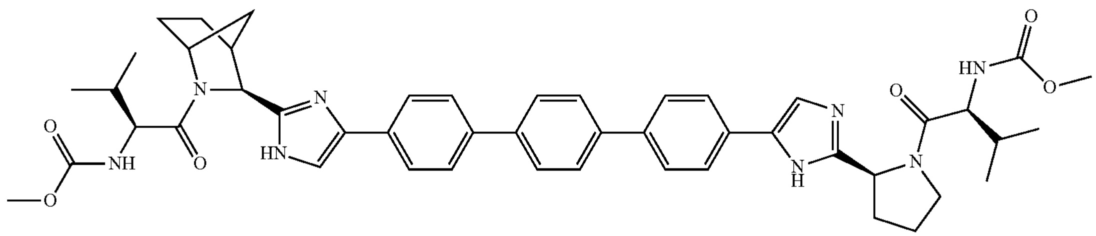 | | |
| 70 | 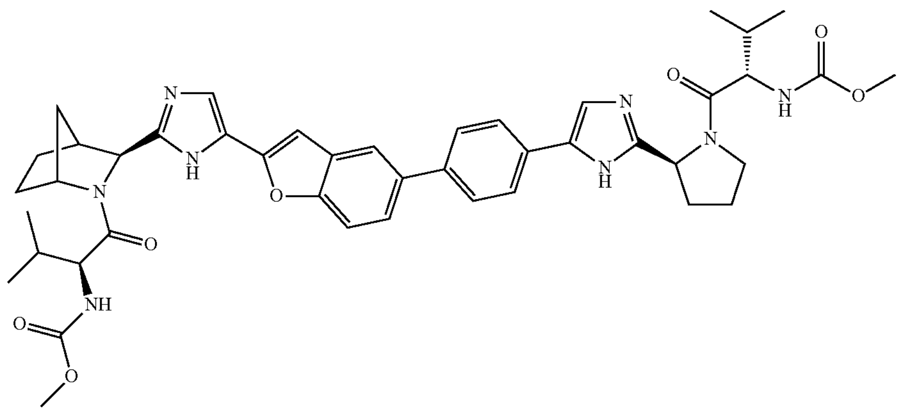 [SMILES: COC(=O)N[C@H](C(=O)N1CCC[C@H]1c1ncc(-c2ccc(-c3ccc4oc(-c5cnc([C@@H]6C7CCC(C7)N6C(=O)[C@@H](NC(=O)OC)C(C)C)[nH]5)cc4c3)cc2)[nH]1)C(C)C] | | *** |

-continued

| Cmp. | Structure | Name | EC50 (uM) |
|---|---|---|---|
| 71 | 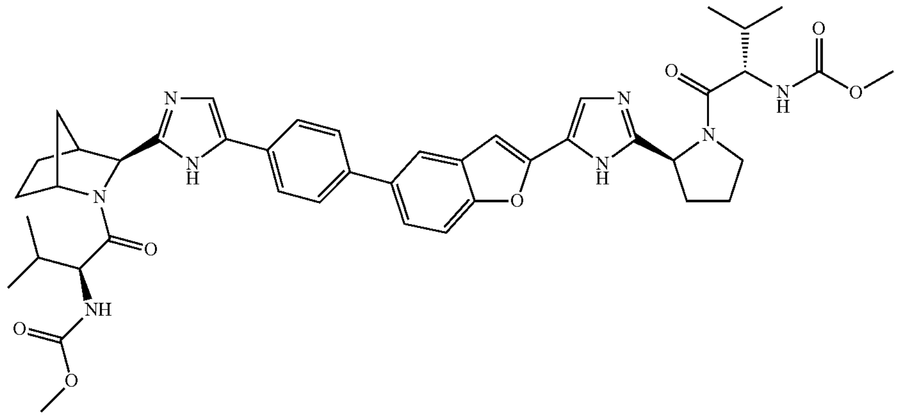 [SMILES: COC(=O)N[C@H](C(=O)N1CCC[C@H]1c1ncc(-c2cc3cc(-c4ccc(-c5cnc([C@@H]6C7CCC(C7)N6C(=O)[C@@H](NC(=O)OC)C(C)C)[nH]5)cc4)ccc3o2)[nH]1)C(C)C] | | *** |
| 72 | 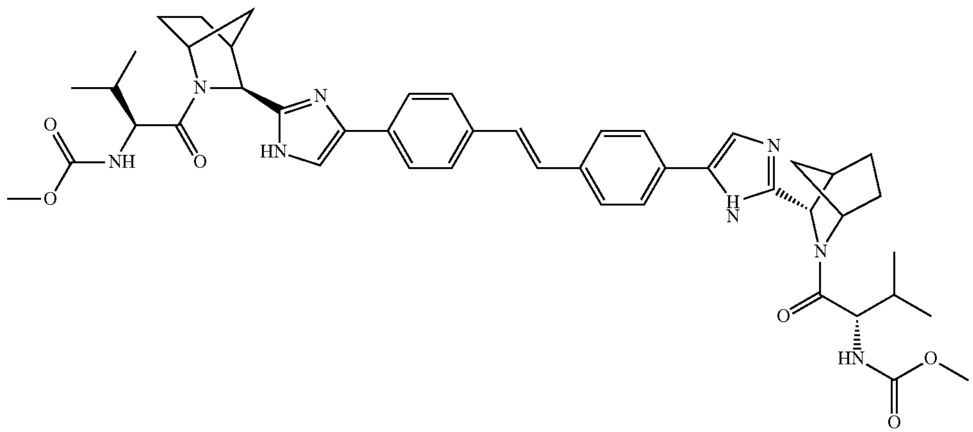 | | *** |

| Cmp. | Structure | Name | EC50 (uM) |
|---|---|---|---|
| 73 | 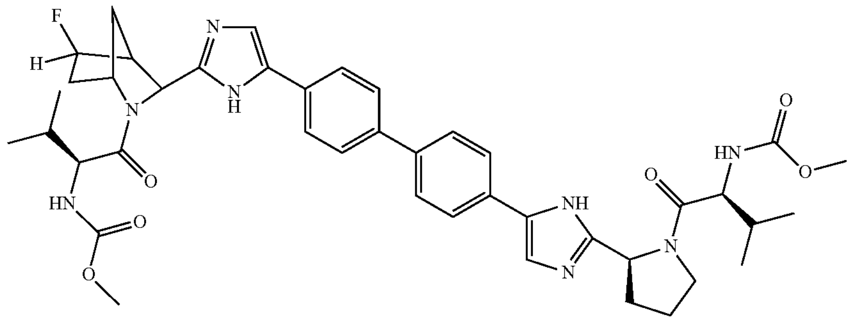 [SMILES: COC(=O)N[C@H](C(=O)N1C2CC(F)C(C2)C1c1ncc(-c2ccc(-c3ccc(-c4cnc([C@@H]5CCCN5C(=O)[C@@H](NC(=O)OC)C(C)C)[nH]4)cc3)cc2)[nH]1)C(C)C] | | *** |
| 74 | 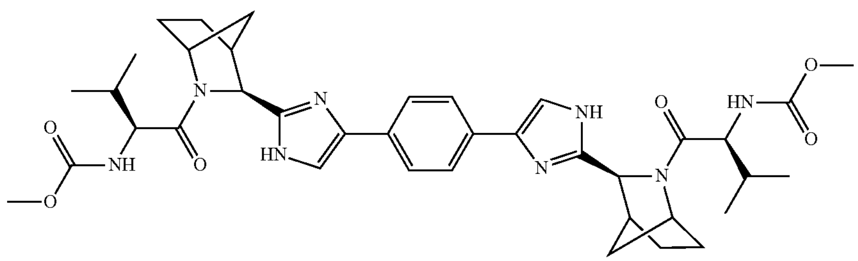 | | ** |
| 75 | 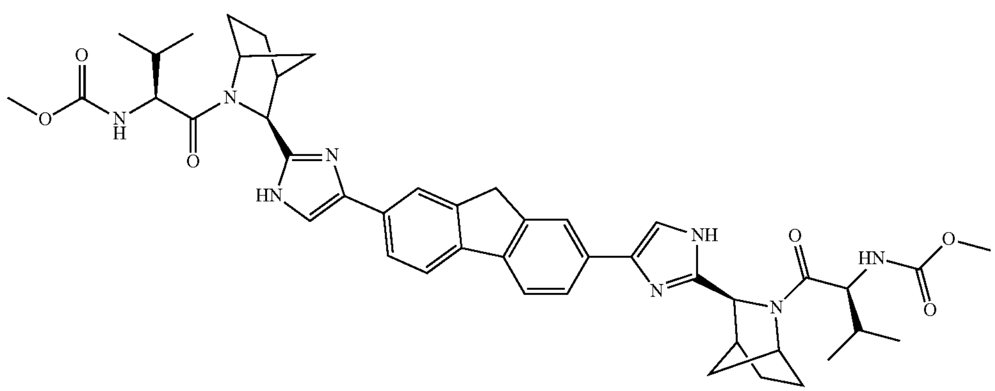 | | *** |

-continued

| Cmp. | Structure | Name | EC50 (uM) |
|---|---|---|---|
| 76 | 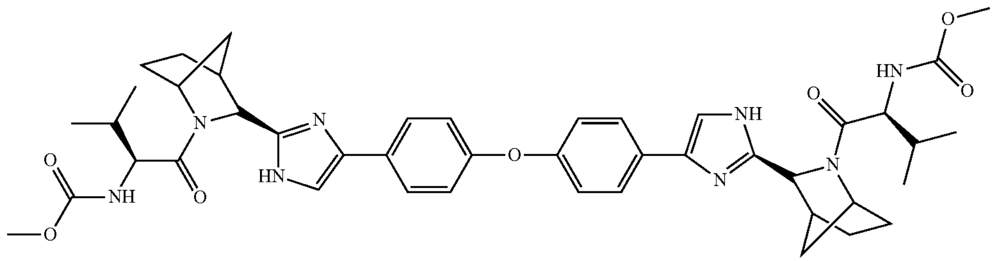 | | |
| 77 | 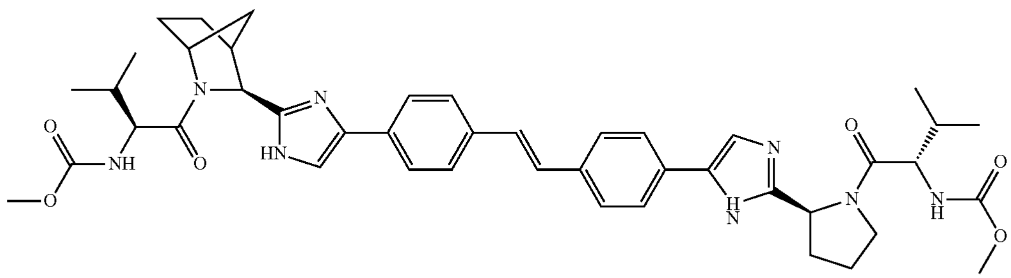 [SMILES: COC(=O)N[C@H](C(=O)N1CCC[C@H]1c1ncc(-c2ccc(/C=C/c3ccc(-c4c[nH]c([C@@H]5C6CCC(C6)N5C(=O)[C@@H](NC(=O)OC)C(C)C)n4)cc3)cc2)[nH]1)C(C)C] | | |
| 78 | 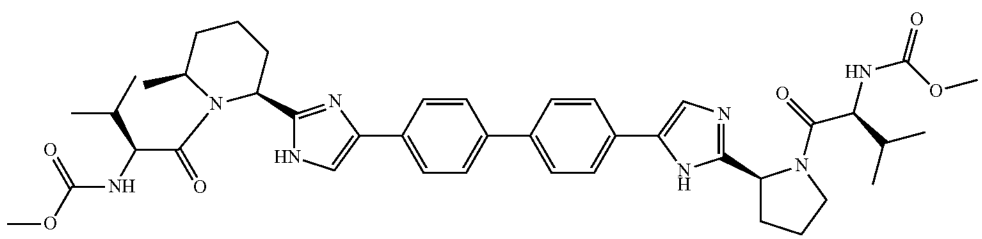 | | |

*EC50 <100 nM,
**EC50 <50 nM,
*** EC50 <5nM

Example 6

Assay for Identifying Compounds which Inhibit HCV Replication

Compounds claimed herein are tested for the ability to inhibit viral replication of the Hepatitis C replicon in cultured cells in which the HCV replicon construct has been incorporated. The HCV replicon system was described by Bartenschlager, et. al (Science, 285, pp. 110-113 (1999)). The replicon system is predictive of in vivo anti-HCV activity; compounds that are active in humans uniformly evidence activity in the replicon assay.

In this assay HCV replicon containing cells are treated with different concentrations of the test compound to ascertain the ability of the test compound to suppress replication of the HCV replicon. As a positive control, HCV replicon-containing cells are treated with different concentrations of interferon alpha, a known inhibitor of HCV replication. The replicon assay system includes Neomycin Phosphotransferase (NPT) as a component of the replicon itself in order to detect the transcription of replicon gene products in the host cell. Cells in which the HCV replicon is actively replicating have high levels of NPT; the level of NPT is proportional to HCV replication. Cells in which the HCV replicon is not replicating also have low levels of NPT and thus do not survive when treated with Neomycin. The NPT level of each sample is measured using a captured ELISA.

A protocol for testing compounds for the ability to inhibit viral replication of the Hepatitis C replicon cultured cells in which the replicon construct has been incorporated, follows.

6A. HCV Replicon and Replicon Expression

The HCV genome consists of a single ORF that encodes a 3000 amino acid polyprotein. The ORF is flanked on the 5' side by an untranslated region that serves as an internal ribosome entry site (IRES) and at the 3' side by a highly conserved sequence necessary for viral replication (3'-NTR). The structural proteins, necessary for viral infection, are located near the 5' end of the ORF. The non-structural proteins, designated NS2 to NS5B comprise the remainder of the ORF.

The HCV replicon contains, 5'-3', the HCV-IRES, the neomycin phosphotransferase (neo) gene, the IRES of encephalomyocarditis virus, which directs translation of HCV sequences NS3 to NS5B, and the 3'-NTR. The sequence of the HCV replicon has been deposited in GenBank (Accession no. AJ242652).

The replicon is transfected into Huh-7 cells using standard methods such as electroporation.

6B. Cell Maintenance

The equipment and materials include, but are not limited to, Huh-7 HCV replicon-containing cells, maintenance media (DMEM (Dulbecco's modified Eagle media) supplemented with 10% FBS, L-glutamine, non-essential amino acids, penicillin (100 units/ml), streptomycin (100 micrograms/ml), and 500 micrograms/ml of Geneticin (G418), screening media (DMEM supplemented with 10% FBS, L-glutamine, non-essential amino acids, penicillin (100 units/ml) and streptomycin (100 micrograms/ml)), 96 well tissue culture plates (flat bottom), 96 well plates (U bottom for drug dilution), Interferon alpha for positive control, fixation reagent (such as methanol: acetone), primary antibody (rabbit anti-NPTII), secondary antibody: Eu-N1 1, and enhancement solution.

HCV replicon-containing cells support high levels of viral RNA replicon replication when their density is suitable. Over-confluency causes decreased viral RNA replication. Therefore, cells must be kept growing in log phase in the presence of 500 micrograms/ml of G418. Generally, cells should be passed twice a week at 1: 4-6 dilution. Cell maintenance is conducted as follows:

HCV replicon-containing cells are examined under a microscope to ensure that cells growing well. Cells are rinsed once with PBS and 2 ml trypsin is added. The cell/trypsin mixture is incubated at 37° C. in a CO2 incubator for 3-5 minutes. After incubation 10 ml of complete media is added to stop the trypsinization reaction. Cells are blown gently, put into a 15 ml tube, and spun at 1200 rpm for 4 minutes. The trypsin/medium solution is removed. Medium (5 ml) is added and the cells are mixed carefully. The cells are counted.

The cells are then seeded onto 96-well plates at a density of 6000-7500 cells/100 microliters/well (6–7.5×105 cells/10 ml/plate). The plates are then incubated at 37° C. in a 5% CO2 incubator.

Cells are examined under a microscope approximated 24 hours after seeding and prior to adding drugs. If counting and dilution were performed correctly, cells are 60-70% confluent and nearly all cells should attach and spread evenly in the well.

6C. Treatment of HCV-Replicon Containing Cells with Test Compound

HCV replicon-containing cells are rinsed with once PBS once; 2 mls of trypsin are then added. Cells are incubated at 37° C. in a 5% CO2 incubator for 3-5 minutes. 10 mls of complete medium is added to stop the reaction. Cells are blown gently, put into a 15 ml tube, and spun at 1200 rpm for four minutes. The trypsin/medium solution is removed and 5 mls of medium (500 ml DMEM (high glucose)) from BRL catalog #12430-054; 50 mls 10% FBS, 5% Geneticin G418 (50 mg/ml, BRL catalog #10131-035), 5 ml MEM non-essential amino acids (100× BRL #11140-050) and 5 ml penstrep (BRL #15140-148) is added. The cells and media are mixed carefully Cells are plated with screening medium (500 ml DMEM (BRL #21063-029), 50 ml FBS (BRL #10082-147) and 5 ml MEM non-essential amino acid (BRL #11140-050) at 6000-7500 fcells/100 µl/well of 96 well plate (6–7.5×105 cells/10 ml/plate). Plates are placed into 37° C. 5% CO2 incubator overnight.

6D. Assay

The following morning, drugs (test compounds or interferon alpha) are diluted in 96 well U bottom plates with media or DMSO/media, depending on the final concentration chosen for screening. Generally for 6 concentrations of each test compounds ranging from 10 micromolar to 0.03 micromolar are applied. 100 µl of the test compound dilution is placed in wells of the 96 well plate containing the HCV replicon cells. Media without drug is added to some wells as a negative controls. DMSO is known to affect cell growth. Therefore, if drugs diluted in DMSO are used, all wells, including negative control (media only) and positive control (interferon alpha) wells, must contain the same concentration of DMSO, for single dose screening. The plates are incubated at 37° C. in a humidified 5% CO2 environment for three days.

On day four, the NTPII assay is quantitated. The medium is poured from the plates and the plates are washed once in 200 µl of PBS. The PBS is then decanted and the plates tapped in a paper towel to remove any remaining PBS. Cells are fixed in situ with 100 µl/well of pre-cooled (−20° C.) methanol:acetone (1:1) and the plates are placed at −20° C. for 30 minutes.

The fixing solution is poured from the plates and the plates allowed to air-dry completely (approximately one hour). The appearance of the dried cell layer is recorded and the density of the cells in the toxic wells is scored with the naked eye. Alternatively cell viability may be assessed using the MTS assay described below.

The wells are blocked with 200 µl of blocking solution (10% FBS; 3% NGS in PBS) for 30 minutes at room temperature. The blocking solution is removed and 100 µl of rabbit anti-NPTII diluted 1:1000 in blocking solution is added to each well. The plates are then incubated 45-60 minutes at room temperature. After incubation, wells are washed six times with PBS-0.05% Tween-20 solution. 100 µl of 1:15,000 diluted Europium (EU)-conjugated goat anti-rabbit in blocking buffer is added to each well and incubated at room temperature for 30-45 minutes. The plates are washed again and 100 µl of enhancement solution (Perkin Elmer #4001-0010) is added to each well. Each plate is shaken (approx. 30 rpm) in a plate shaker for three minutes. 95 µl is transferred from each well to a black plate; the EU signal is quantitated in a Perkin-Elmer VICTOR plate reader (EU-Lance).

When tested in this assay Compounds 11, 16, 25, 33, 38, 39, and 40 exhibit EC50 values of about 10 micromolar or less.

Example 7

Cytotoxicity Assays

To insure that the decrease in replicon replication is due to compound activity against the HCV replicon rather than non-specific toxicity assays are used to quantitate compound cytotoxicity.

7A. Cellular Protein Albumin Assay for Cytotoxicity

Cellular protein albumin measurements provide one marker of cytotoxicity. The protein levels obtained from cellular albumin assays may also be used to provide a normalization reference for antiviral activity of compounds. In the protein albumin assay HCV replicon-containing cells are treated for three days with different concentrations of helioxanthin; a compound that is known to be cytotoxic at high concentrations. The cells are lysed and the cell lysate used to bind plate-bound goat anti-albumin antibody at room temperature (25° C. to 28° C.) for 3 hours. The plate is then washed 6 times with 1× PBS. After washing away the unbound proteins, mouse monoclonal anti-human serum albumin is applied to bind the albumin on the plate. The complex is then detected using phosphatase-labeled anti-mouse IgG as a second antibody.

7B. MTS Assay for Cytotoxicity

Cell viability may also be determined by CELLTITER 96 AQUEOUS ONE Solution Cell Proliferation Assay (Promega, Madison Wis.), a colorimetric assay for determining the number of viable cells. In this method, before fixing the cells, 10-20 µl MTS reagent is added to each well according to manufacturer's instructions, plates are incubated at 37° C. and read at OD 490 nm. During the incubation period living cells covert the MTS reagent to a formazan product which absorbs at 490 nm. Thus the 490 nm absorbance is directly proportional to the number of living cells in culture.

A direct comparison of the Cellular Albumin and MTS methods for determining cytotoxicity may be obtained as follows: Cells are treated with different concentrations of test compound or Helioxanthin for a three day-period. Prior to lysis for detection albumin as described above, the MTS reagent is added according to manufacturer's instruction to each well and incubate at 37° C. and read at OD 490 nm. The cellular albumin quantitation is then performed as described above.

What is claimed is:

1. A pharmaceutical composition of a compound of Formula II or pharmaceutically acceptable salt thereof together with a compound of Formula III or a pharmaceutically acceptable salt thereof, wherein the compound of Formula II is

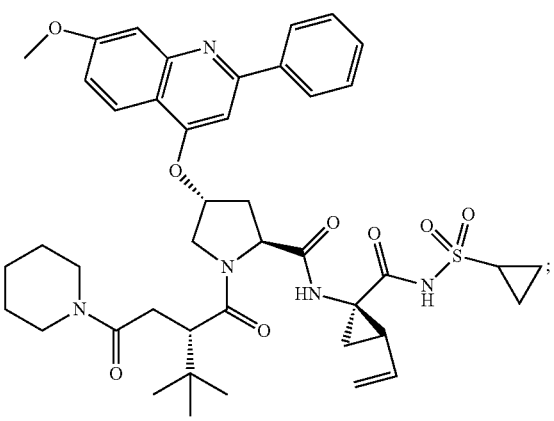

and the compound of Formula III is

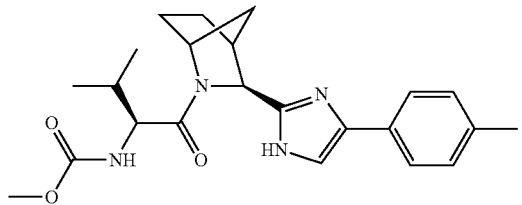

2. A pharmaceutical composition of claim 1, additionally comprising a pharmaceutically acceptable carrier.

3. The pharmaceutical composition of claim 1, wherein the composition comprises at least one additional active agent, wherein the additional active agent is a nucleoside analogue.

4. The pharmaceutical composition of claim 2, wherein the molar ratio of the compound of Formula II to the compound of Formula III is from about 2:1 to about 4:1.

5. A method of treating an HCV infection in a patient, comprising providing a therapeutically effective amount of a compound or salt of Formula II and a therapeutically effective amount of a compound or salt of Formula III to the patient, wherein the compound of Formula II is

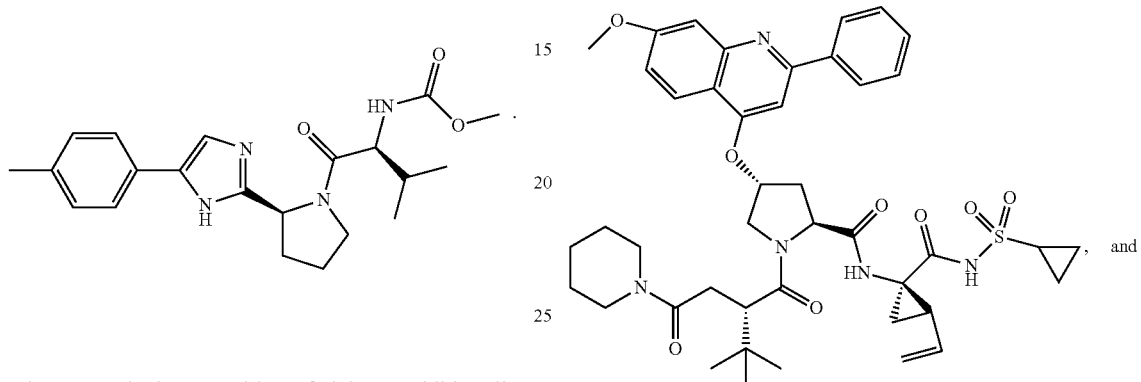

the compound of Formula III is:

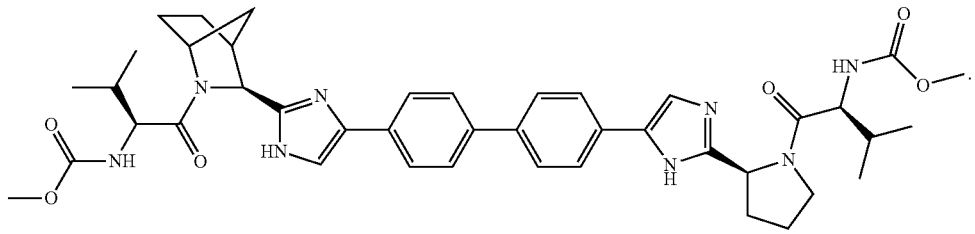

6. The pharmaceutical composition of claim 2, wherein the molar ratio of the compound of Formula II to the compound of Formula III is about 2:1 or greater.

7. A method of treating an HCV infection in a patient, comprising providing a therapeutically effective amount of a pharmaceutical composition of claim 1 to the patient.

* * * * *